(12) United States Patent
Yarlagadda et al.

(10) Patent No.: US 11,449,994 B2
(45) Date of Patent: Sep. 20, 2022

(54) MACHINE LEARNING MODEL FOR ANALYZING PATHOLOGY DATA FROM METASTATIC SITES

(71) Applicant: MEMORIAL SLOAN KETTERING CANCER CENTER, New York, NY (US)

(72) Inventors: Dig Vijay Kumar Yarlagadda, New York, NY (US); Matthew Hanna, New York, NY (US); Peter Schueffler, New York, NY (US); Thomas Fuchs, New York, NY (US)

(73) Assignee: MEMORIAL SLOAN KETTERING CANCER CENTER, New York, NY (US)

( * ) Notice: Subject to any disclaimer, the term of this patent is extended or adjusted under 35 U.S.C. 154(b) by 0 days.

(21) Appl. No.: 17/335,925

(22) Filed: Jun. 1, 2021

(65) Prior Publication Data

US 2021/0374954 A1 Dec. 2, 2021

Related U.S. Application Data

(60) Provisional application No. 63/033,730, filed on Jun. 2, 2020.

(51) Int. Cl.
| | |
|---|---|
| *G06T 7/00* | (2017.01) |
| *G06K 9/62* | (2022.01) |
| *G06T 7/73* | (2017.01) |
| *G06N 20/00* | (2019.01) |

(Continued)

(52) U.S. Cl.
CPC ............ *G06T 7/0012* (2013.01); *G06K 9/623* (2013.01); *G06K 9/6232* (2013.01); *G06K 9/6257* (2013.01); *G06K 9/6265* (2013.01);

*G06N 20/00* (2019.01); *G06T 7/73* (2017.01); *G16H 30/40* (2018.01); *G16H 70/60* (2018.01); *G06T 2207/20084* (2013.01);

(Continued)

(58) Field of Classification Search
None
See application file for complete search history.

(56) References Cited

U.S. PATENT DOCUMENTS

| | | | |
|---|---|---|---|
| 10,769,501 B1 * | 9/2020 | Ando | G01N 33/5005 |
| 11,120,307 B2 * | 9/2021 | Xie | G06K 9/6232 |
| 2011/0123100 A1 | 5/2011 | Carroll et al. | |

(Continued)

OTHER PUBLICATIONS

VOCA: Cell Nuclei Detection in Histopathology Images by Vector Oriented Confidence Accumulation Chensu Xie; Jun. 2019 (Year: 2019).*

(Continued)

*Primary Examiner* — Nancy Bitar
(74) *Attorney, Agent, or Firm* — Foley & Lardner LLP

(57) ABSTRACT

Described herein are systems and methods of determining primary sites from biomedical images. A computing system may identify a first biomedical image of a first sample from one of a primary site or a secondary site associated with a condition in a first subject. The computing system may apply the first biomedical image to a site prediction model comprising a plurality of weights to determine the primary site for the condition. The computing system may store an association between the first biomedical image and the primary site determined using the site prediction model.

20 Claims, 18 Drawing Sheets

(51) Int. Cl.
    *G16H 70/60*     (2018.01)
    *G16H 30/40*     (2018.01)

(52) U.S. Cl.
    CPC ............... *G06T 2207/30024* (2013.01); *G06T 2207/30096* (2013.01); *G06V 2201/03* (2022.01)

(56) References Cited

U.S. PATENT DOCUMENTS

| | | |
|---|---|---|
| 2016/0171682 A1 | 6/2016 | Abedini et al. |
| 2016/0253800 A1 | 9/2016 | Gurevich et al. |
| 2016/0275374 A1* | 9/2016 | Zhu ..................... G06K 9/6267 |
| 2017/0161891 A1* | 6/2017 | Madabhushi ........ G06K 9/4642 |
| 2017/0169276 A1 | 6/2017 | Agaian et al. |
| 2019/0087954 A1 | 3/2019 | Lloyd et al. |
| 2019/0220701 A1* | 7/2019 | Novak .................. A61B 6/5211 |
| 2020/0035350 A1* | 1/2020 | Sullivan ................ G16H 50/20 |

OTHER PUBLICATIONS

Multi-Resolution Networks for Semantic Segmentation in Whole Slide Images ; Feng Gu et al ; Jul. 25, 2018 (Year: 2018).*
International Search Report and Written Opinion on PCT PCT/US2021/035133 dated Sep. 23, 2021.

* cited by examiner

MACHINE LEARNING MODEL FOR ANALYZING PATHOLOGY DATA FROM METASTATIC SITES

CROSS-REFERENCE TO RELATED APPLICATIONS

The present application claims priority to U.S. Provisional Application No. 63/033,730, titled "Machine Learning Model for Analyzing Pathology Data from Metastatic Sites," filed Jun. 2, 2020, which is incorporated herein by reference in its entirety.

BACKGROUND

A computing device may use various computer vision algorithms to recognize and detect various features in images. The computing device may also determine characteristics regarding the features within the images.

SUMMARY

Aspects of the present disclosure are directed to systems and methods of determining primary sites from biomedical images. A computing system may identify a first biomedical image of a first sample from one of a primary site or a secondary site associated with a condition in a first subject. The computing system may apply the first biomedical image to a site prediction model comprising a plurality of weights to determine the primary site for the condition. The site prediction model may be trained using a training dataset having a plurality of examples. Each example may include: a second biomedical image of a second sample from one of the primary site or the secondary site of the condition in a second subject from which the second sample is obtained, a first label identifying one of the primary site or the secondary site for the second sample from which the second biomedical image is obtained, and a second label identifying the primary site for the condition in the second subject. The computing system may store an association between the first biomedical image and the primary site determined using the site prediction model.

In some embodiments, the computing system may provide the association between the first biomedical image and the primary site. In some embodiments, the computing system may apply the first biomedical image to the site prediction model to determine a plurality of candidate primary sites for the condition in the first subject.

In some embodiments, the computing system may apply the first biomedical image to the site prediction model to determine a confidence score for the primary site for the condition. In some embodiments, the computing system may apply the first biomedical image to the site prediction model to determine a ranking for the plurality of candidate primary sites.

In some embodiments, the computing system may obtain the first biomedical image of the first sample via a histological image preparer. In some embodiments, the plurality of weights in the site prediction model may be arranged into (i) a plurality of convolution blocks to generate a plurality of feature maps from the biomedical image and (ii) an activation layer to determine the primary site for the condition based on the plurality of feature maps.

Aspects of the present disclosure are directed to systems and methods of training models to determine primary sites from biomedical images. A computing system may identify a training dataset having a plurality of examples. Each example of the plurality of examples may include: a biomedical image of a sample from one of the primary site or the secondary site of the condition in a second subject from which the sample is obtained, a first label identifying one of the primary site or the secondary site for the second sample from which the biomedical image is obtained, a second label identifying the primary site for the condition in the second subject. The computing system may apply the biomedical image in each of the plurality of examples of the training dataset to a site prediction model comprising a plurality of weights to determine a site for the condition of the sample. The computing system may compare, for each example of the plurality of examples in the training dataset, the primary site identified in the label of the example and the site determined by the site prediction model. The computing system may update at least one of the plurality of weights in the site prediction model based on the comparison between the first site identified in the label of each example and the second site determined by the site prediction model. The computing system may store, in one or more data structures, the plurality of weights in the site prediction model.

In some embodiments, the computing system may apply an acquired biomedical image of a second sample to the site prediction model to determine a second site for the second sample. In some embodiments, the computing system may reapply the biomedical image of at least one example of the plurality of examples to the site prediction model, responsive to determining that a loss metric for the at least one example exceeds a threshold.

In some embodiments, the computing system may update at least one of the plurality of weights in the site prediction model using a classification loss determined based on the comparison. In some embodiments, the computing system may apply the biomedical image in each of the plurality of examples of the training dataset to determine a plurality of candidate primary sites for the condition in the first subject.

In some embodiments, the computing system may apply the biomedical image in each of the plurality of examples of the training dataset to determine a confidence score for the primary site for the condition. In some embodiments, the plurality of weights in the site prediction model may be arranged into (i) a plurality of convolution blocks to generate a plurality of feature maps from the biomedical image and (ii) an activation layer to determine the primary site for the condition based on the plurality of feature maps.

BRIEF DESCRIPTION OF THE DRAWINGS

The foregoing and other objects, aspects, features, and advantages of the disclosure will become more apparent and better understood by referring to the following description taken in conjunction with the accompanying drawings, in which:

FIGS. 1B-1 and 1B-2 depict a block diagram of an overview of a process for training a model for identification of a primary site of origin in metastatic sites using whole slide images in accordance with an illustrative embodiment;

FIG. 2 depicts a block diagram of a system for determining primary sites from biomedical images in accordance with an illustrative embodiment;

FIG. 3 depicts a block diagram of a training process for a site prediction model in a system for determining primary sites from biomedical images in accordance with an illustrative embodiment;

FIG. 5 depicts a block diagram of an inference process for a site prediction model in a system for determining primary sites from biomedical images in accordance with an illustrative embodiment;

FIG. 7 depicts a block diagram of a server system and a client computer system in accordance with an illustrative embodiment.

DETAILED DESCRIPTION

Following below are more detailed descriptions of various concepts related to, and embodiments of, systems and methods for determining primary sites from biomedical images. It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

Section A describes systems and methods for determining primary sites from biomedical images; and Section B describes a network environment and computing environment which may be useful for practicing various computing related embodiments described herein.

A. Systems and Methods of Determining Primary Sites of Biomedical Images

Cancerous cells may originate from a primary site and spread to one or more secondary sites (also referred herein as metastatic sites) throughout a body of a subject. Depending on the tumor site, the cancerous cells at the secondary site may appear characteristically similar to those in the primary site of originate. An estimate of the primary site may be a critical factor in devising treatments to alleviate and suppress the spread of cancer in the body. A pathologist may manually examine a whole slide image of tissues from the subject to determine the primary site of origin for the cancer. This process, however, may be slow and cumbersome especially when large numbers of images from multiple subjects are to be examined. Furthermore, the manual nature of the examination may lead to inaccurate diagnoses, resulting in incorrect treatment recommendations. One approach to account for some of these problems may be to use computer vision techniques to recognize cancerous cells within a given tissue depicted in the whole slide image. But this approach may fail to address at providing an estimate of the primary site for the cancerous cells. To address these and other challenges, a model may be trained to learn morphological patterns to predict primary sites of cancerous cells based on whole slide images. The model may identify morphological patterns that are highly correlated with metastatic risk.

Figures 1, 1A:
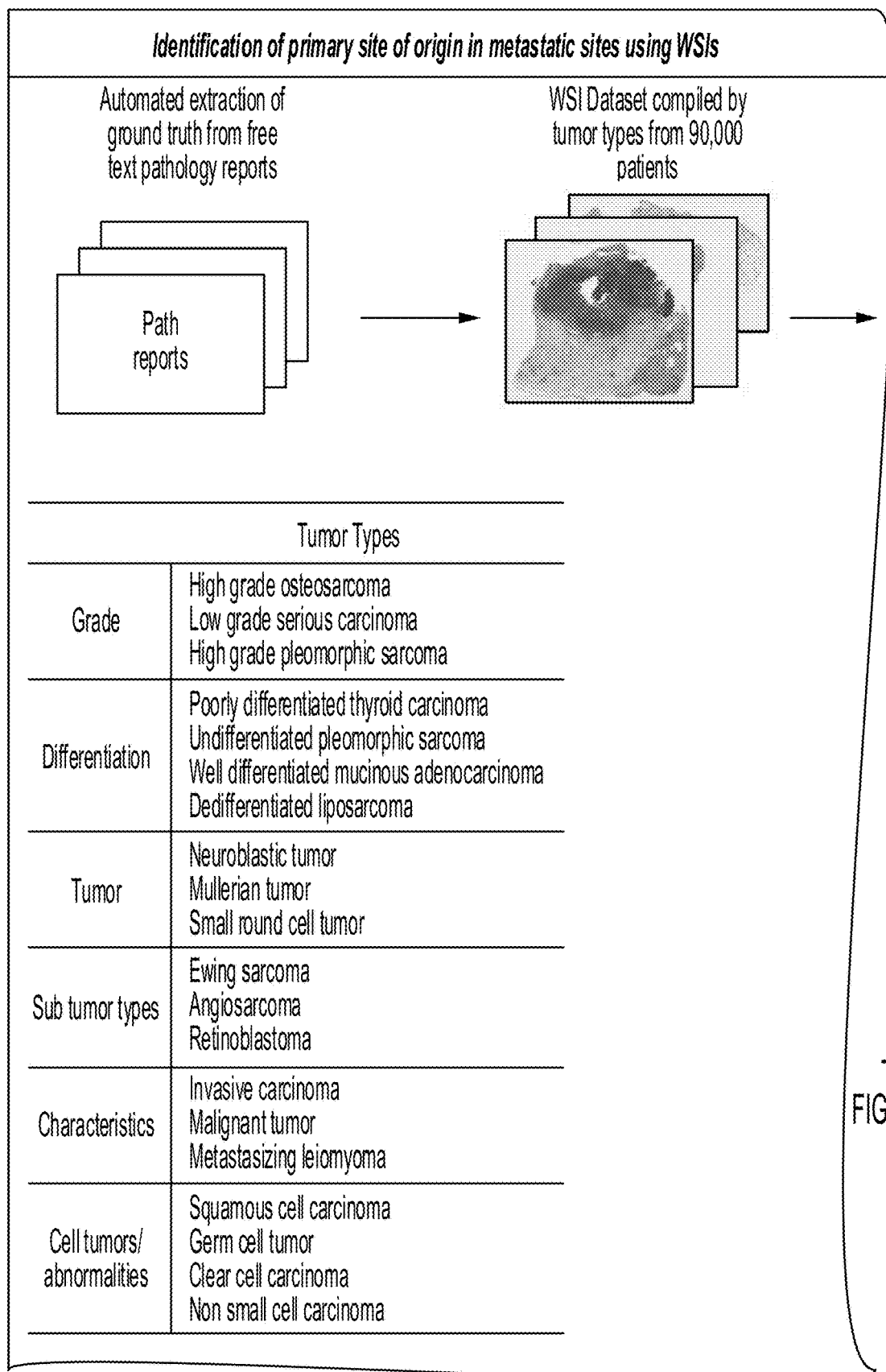
FIGS. 1A-1 to 1A-7 depict a block diagram of an overview of a process for identification of a primary site of origin in metastatic sites using whole slide images in accordance with an illustrative embodiment.

Referring now to FIG. 1A, depicted is a block diagram of an overview of a process 100 for identification of a primary site of origin in metastatic sites using whole slide images. As depicted, ground truth may be automatically extracted from data records of pathology records. The path reports may include tumor types, such as gradation (e.g., high grade osteosarcoma, low-grade serious carcinoma, or high-grade pleomorphic sarcoma), differentiation (e.g., poorly differentiated thyroid carcinoma, undifferentiated pleomorphic sarcoma, well-differentiated mucinous adenocarcinoma, and de-differentiated liposarcoma), tumor (e.g., neuroblastic tumor, Muellerian tumor, and small-round cell tumor), sub-tumor types (e.g., Ewing sarcoma, angiosarcoma, and retinoblastoma), characteristics (e.g., invasive carcinoma, malignant tumor, and metastasizing leiomyoma), and cell tumors or abnormalities (e.g., squamous cell carcinoma, germ cell tumor, clear cell carcinoma, and non-small cell carcinoma), among others. A dataset of whole slide images (WSI) indexed by tumor types may be compiled from several subjects. The tumor regions may be extracted under marker extraction, pathologist annotations, and class activation maps. Using the relevant regions, a classifier may be trained to locate the primary site for the tumor depicted in the image. Additional metastatic risk factors may be analyzed with the prediction of the primary sites from the tissue sample.

Figures 1, 1A, 2:
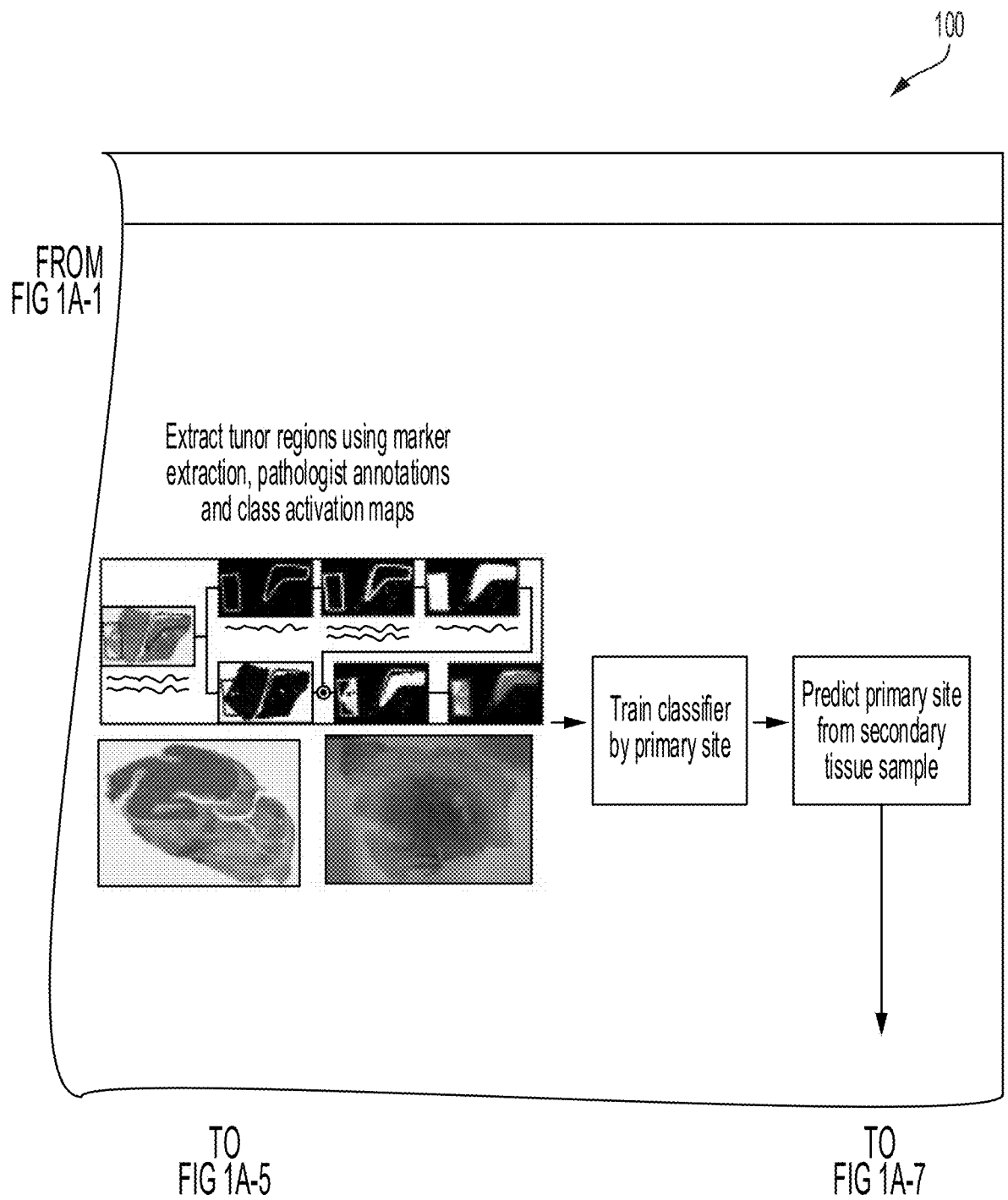
Figures 1, 1A, 2, 3:
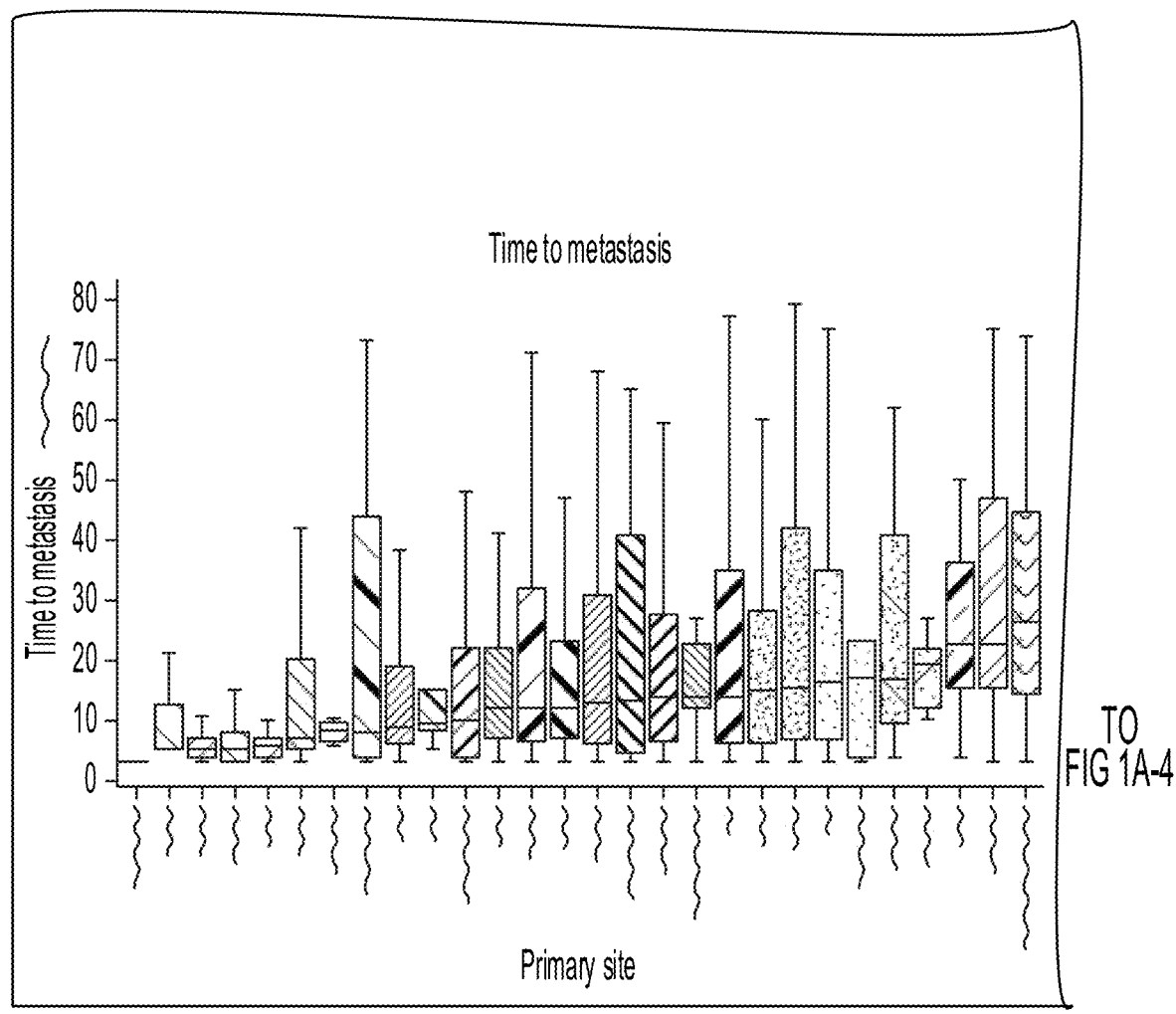
Figures 1, 1A, 2, 3, 4:
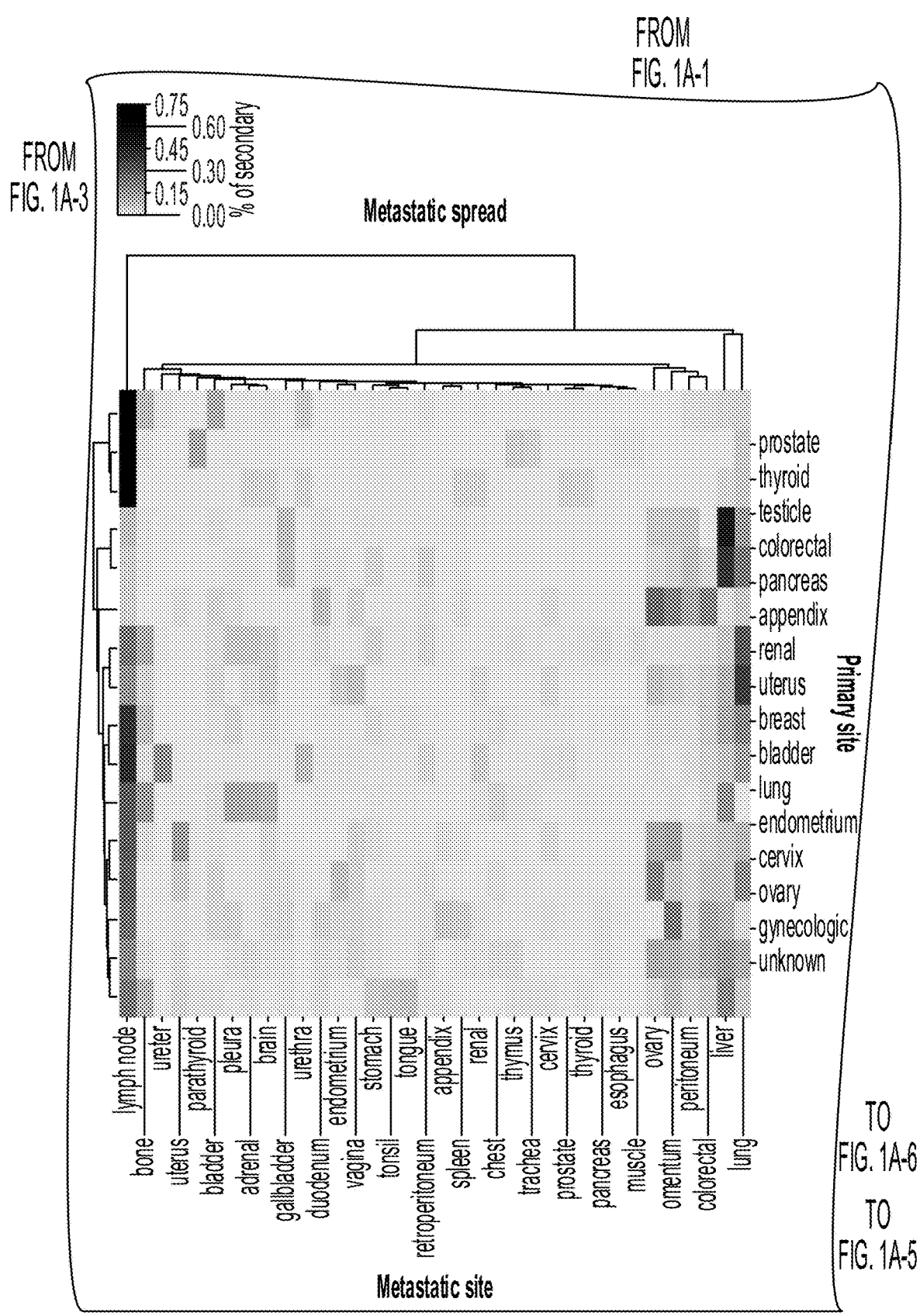
Figures 1, 1A, 2, 3, 4, 5:
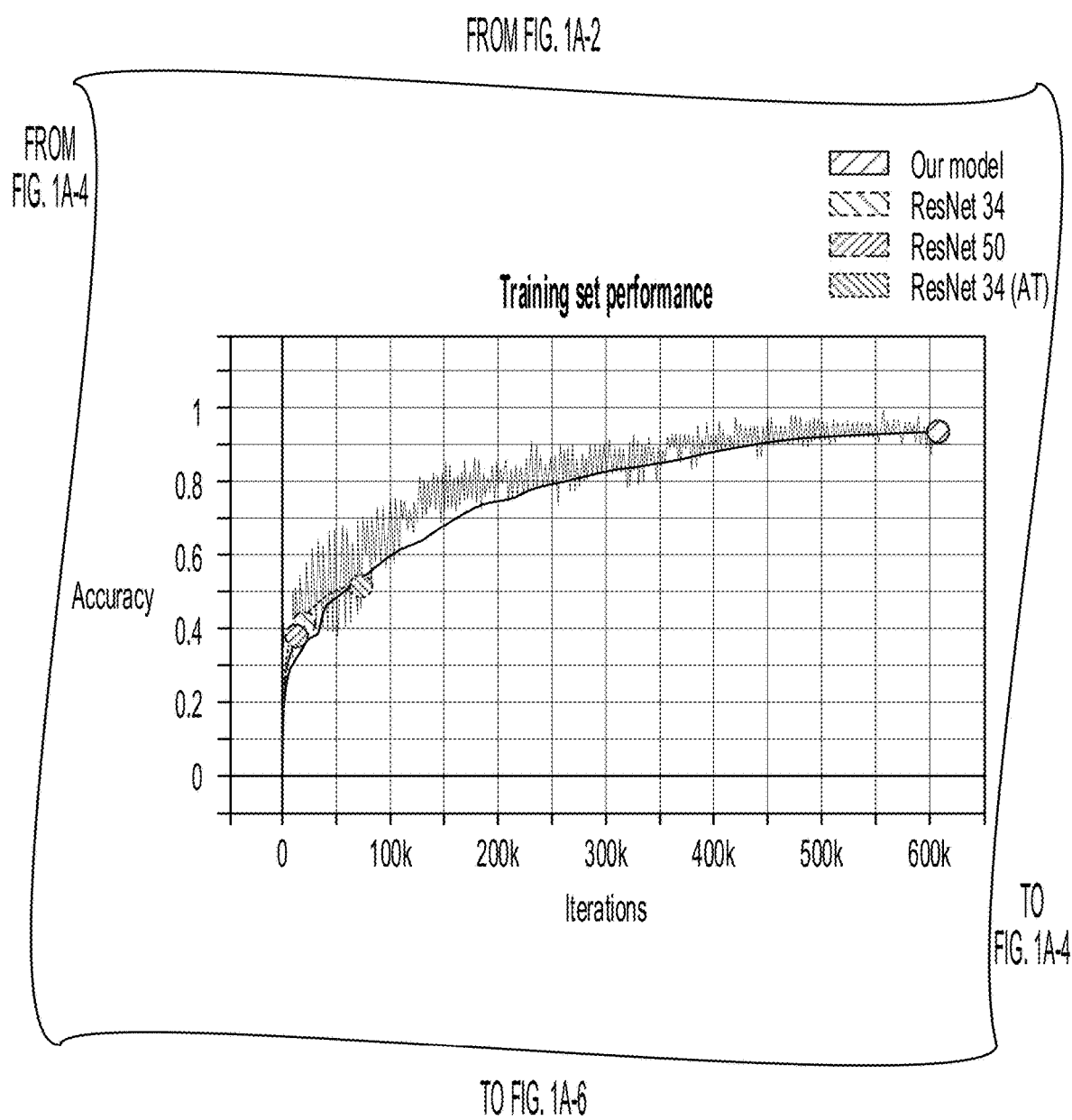
Figures 1, 1A, 2, 3, 4, 5, 6:
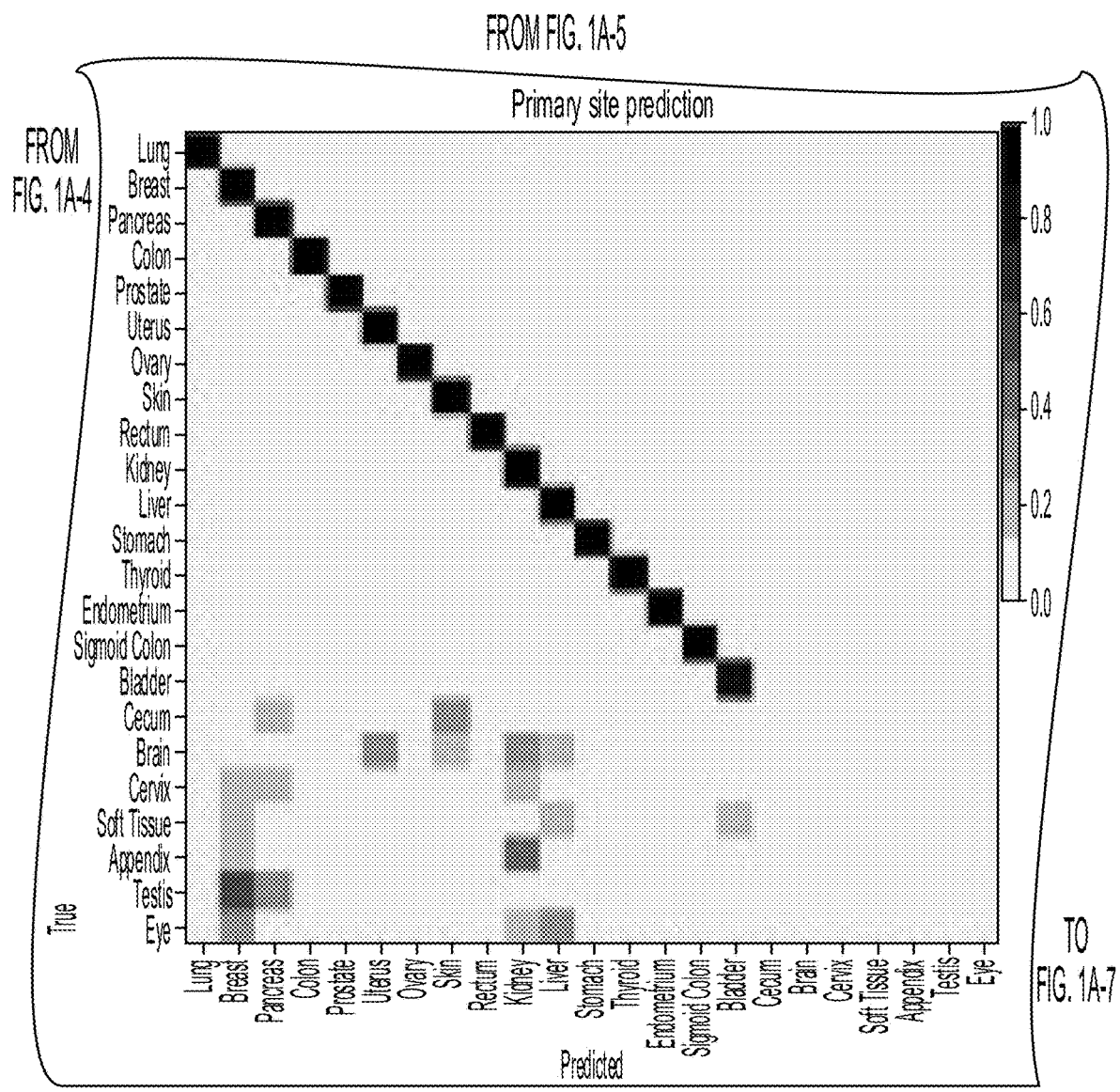
Figures 1, 1A, 2, 3, 4, 5, 6, 7:
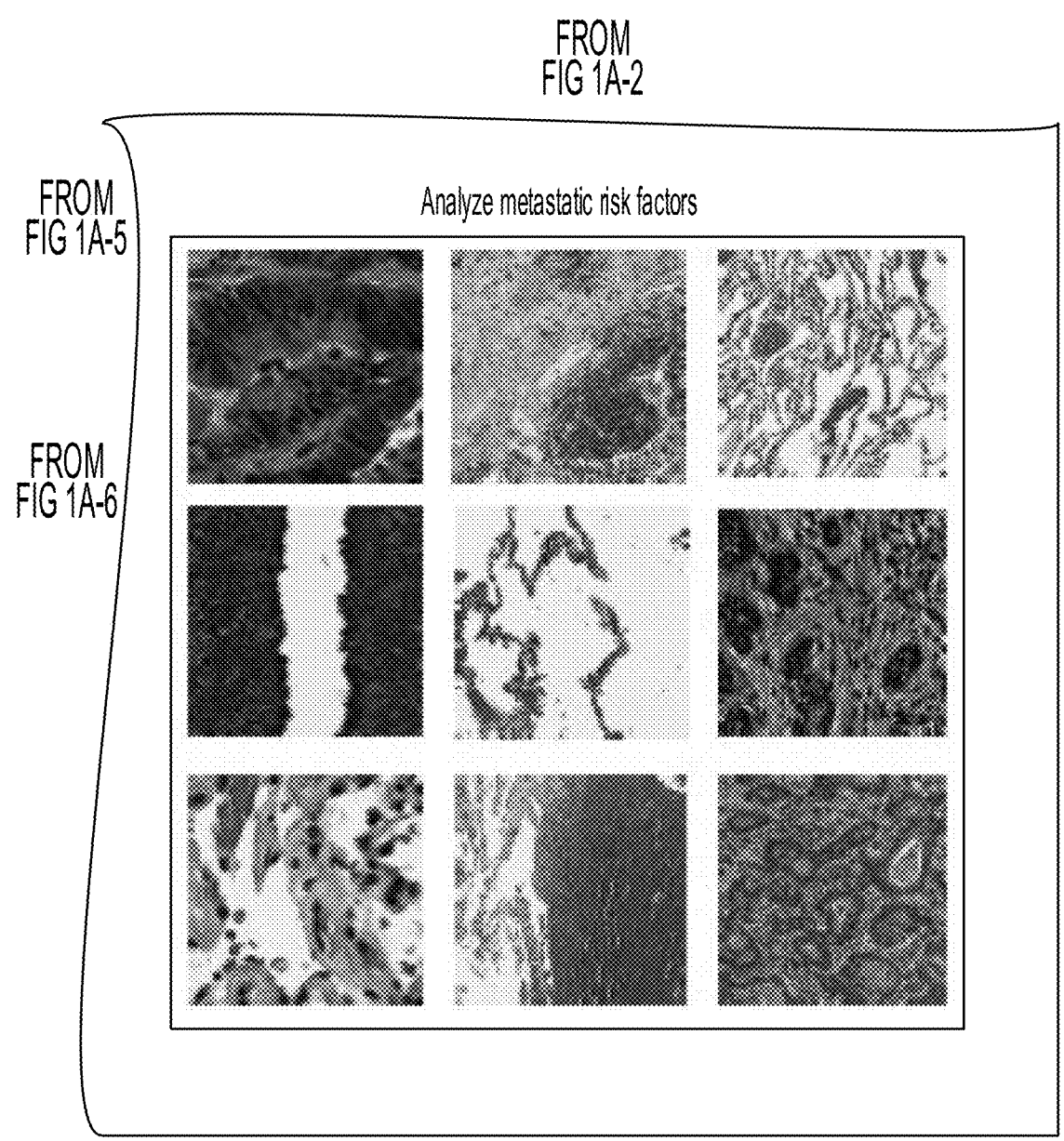
Figures 1, 1B:
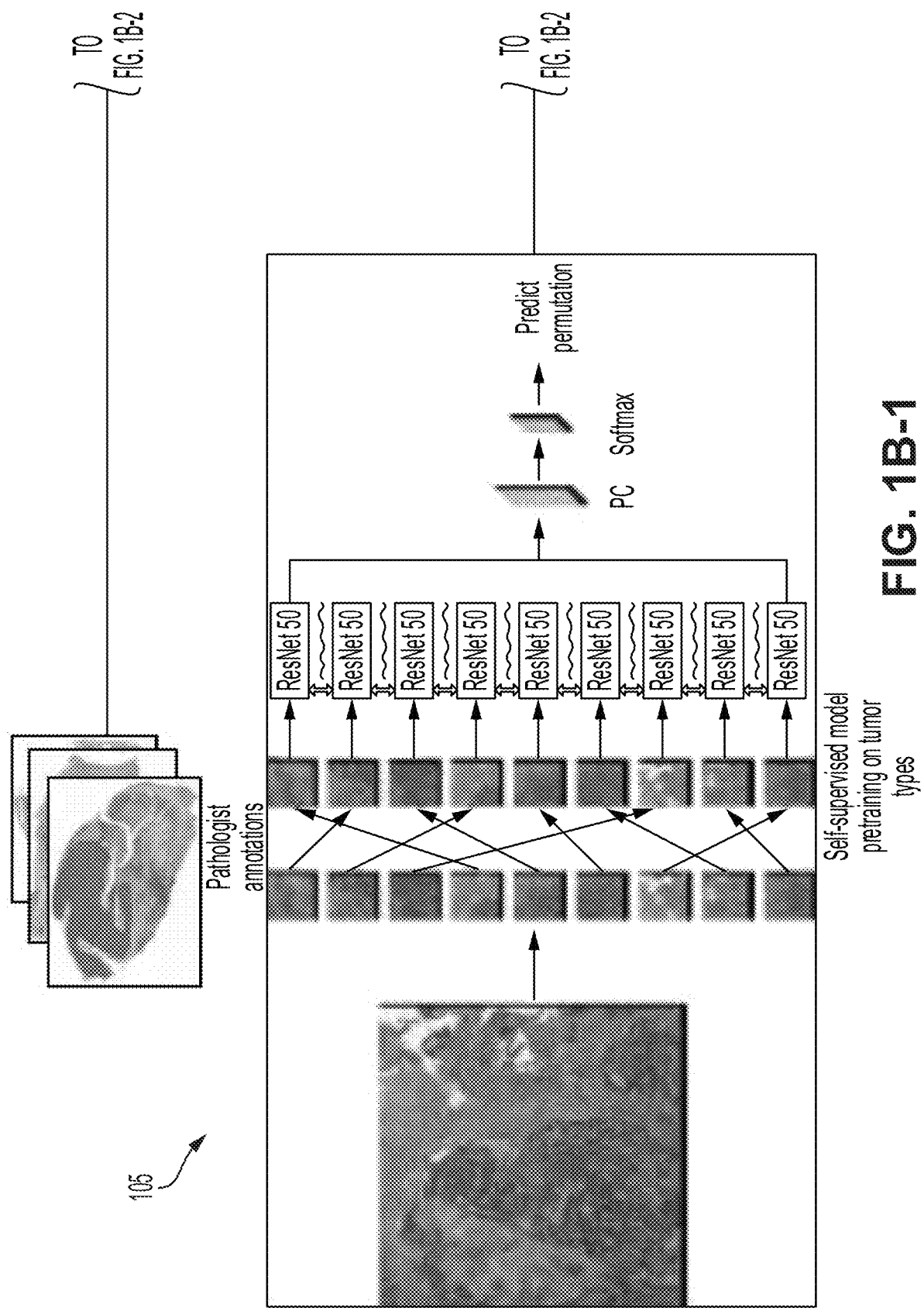
Figures 1, 1B, 2:
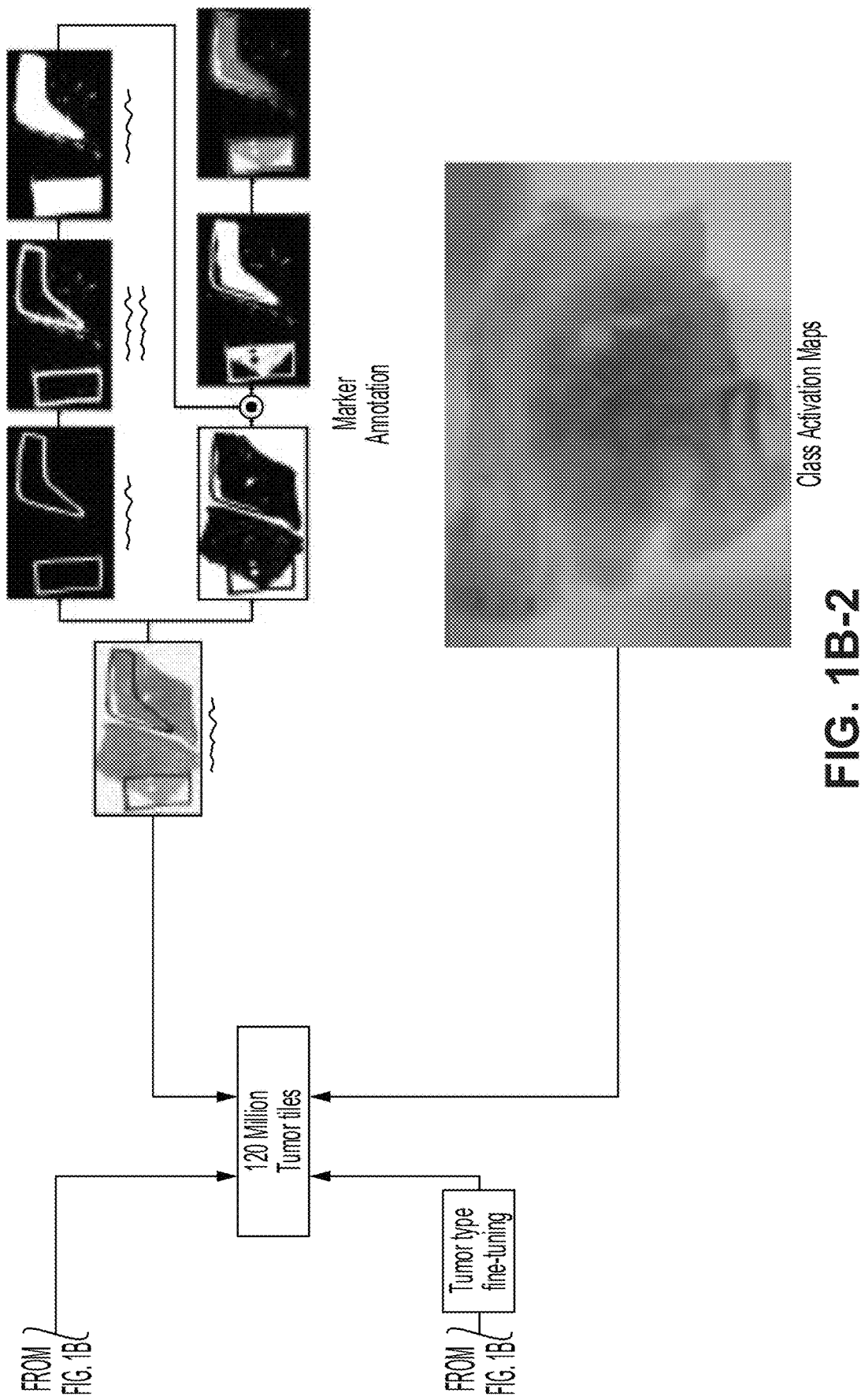
Figure 1C:
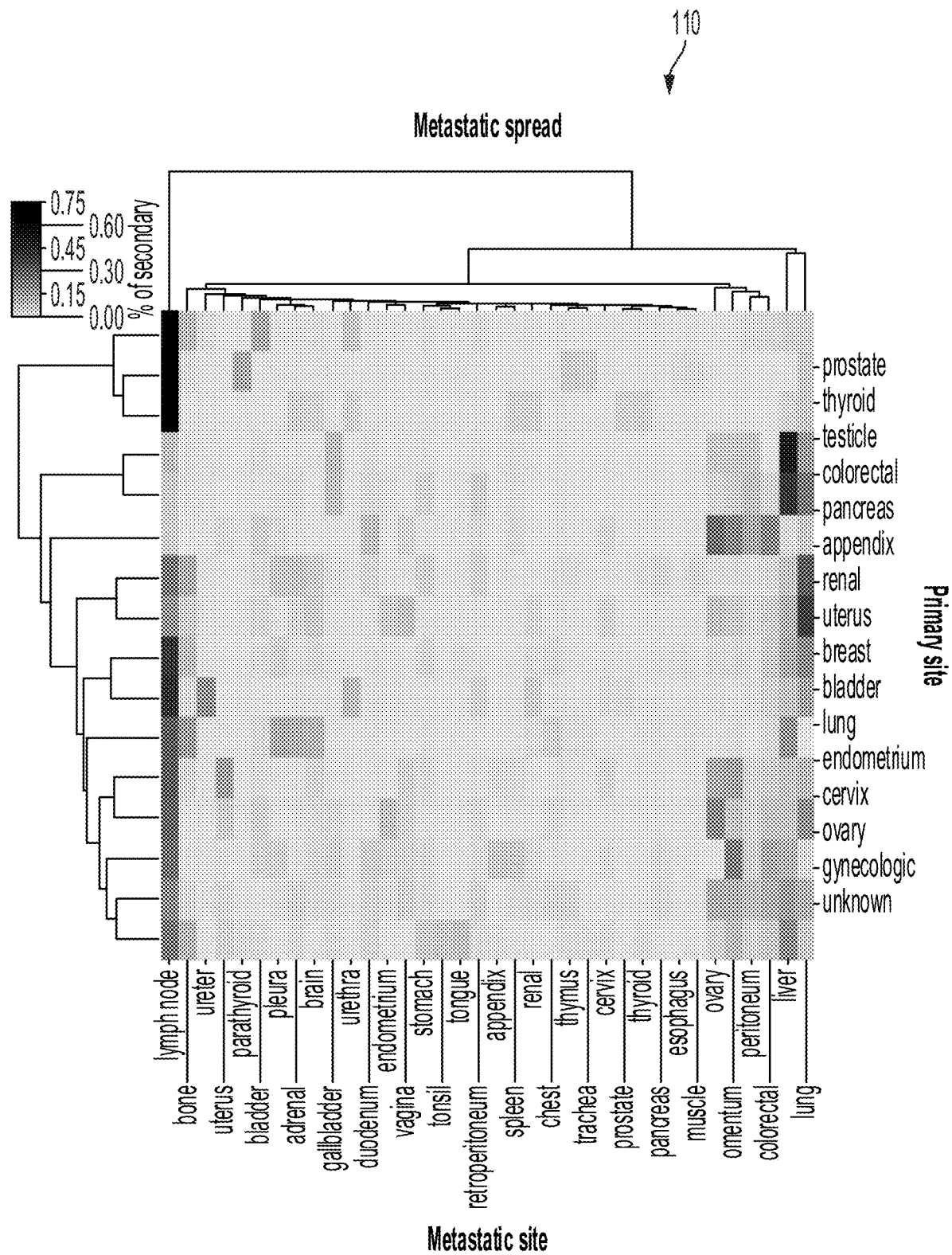
FIG. 1C depicts a graph showing relations between primary sites and metastatic sites in training data used to train the model for identification of primary site of origin in metastatic sites in accordance with an illustrative embodiment.
Figure 2:
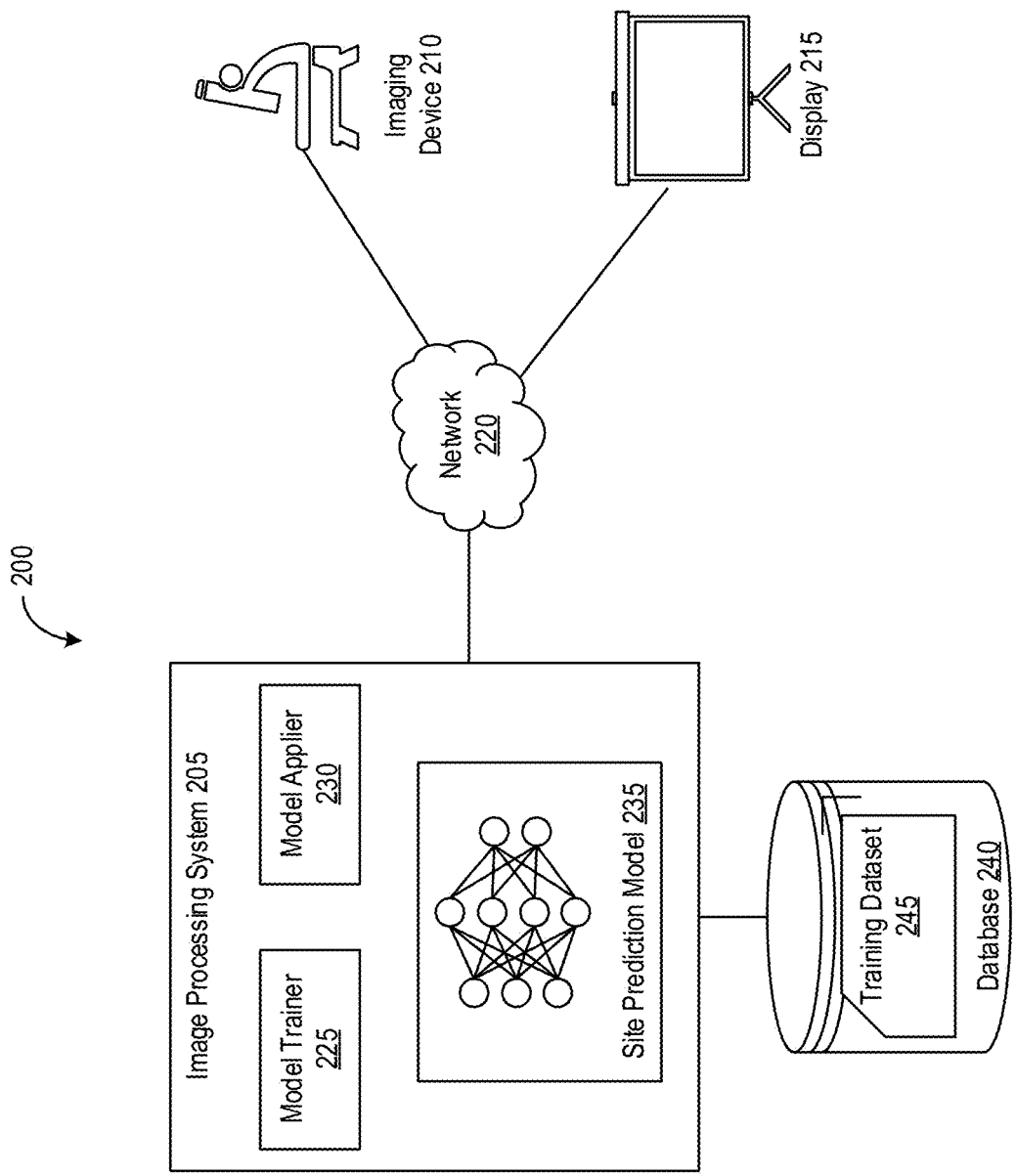
Figure 3:
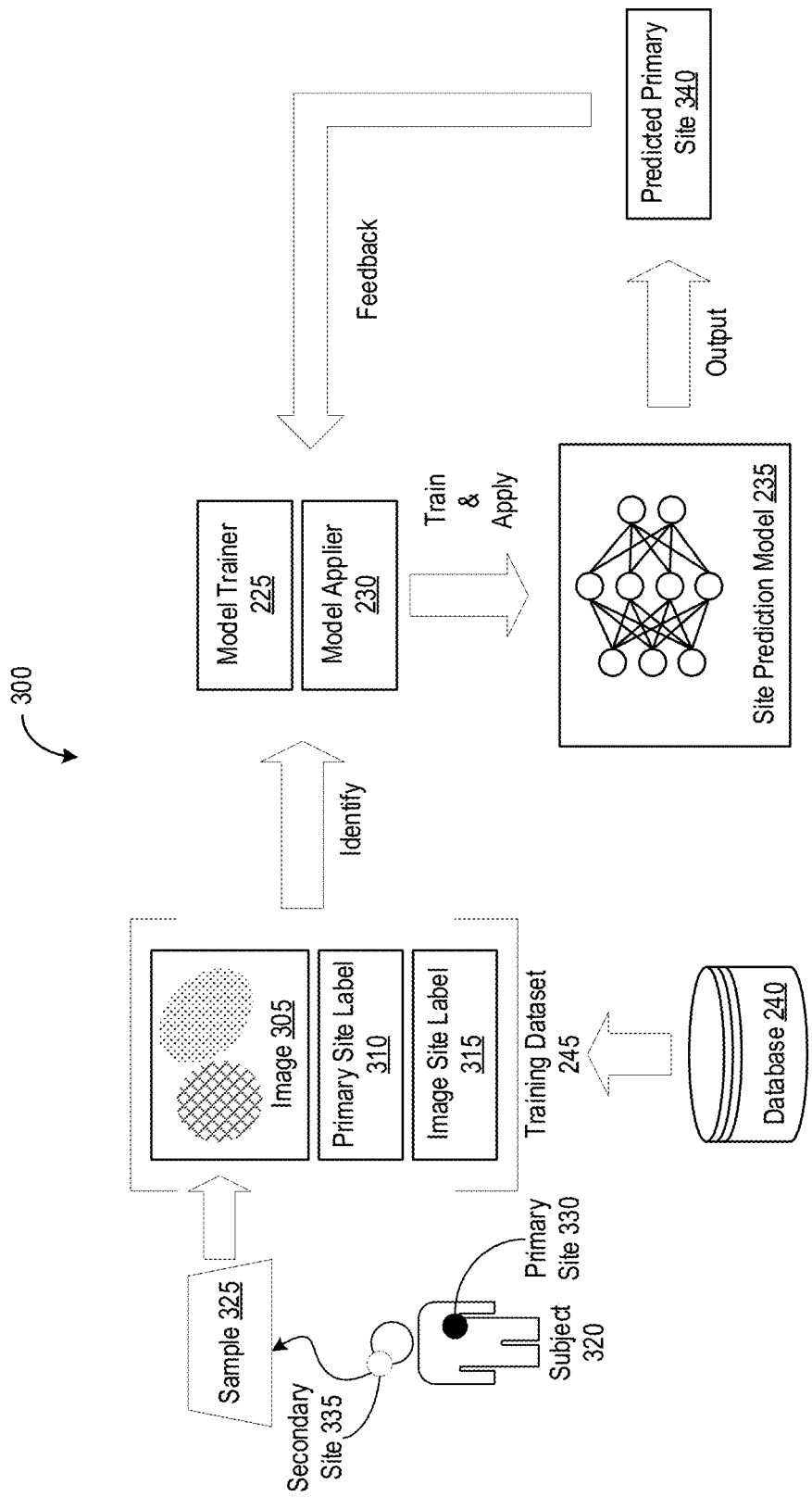

Referring now to FIG. 1B, depicted is a block diagram of an overview a process 105 for training a model for identification of a primary site of origin in metastatic sites using whole slide images. As depicted, a model may be trained using training data in a self-supervised manner. The model may be trained to recognize the tumor types. Marker annotations as well as pathologist annotations may be used to detect the location of the tumorous cell within the whole slide image. Referring now to FIG. 1C, depicted is a graph 110 showing relations between primary sites and metastatic sites in training data used to train the model for identification of primary site of origin in metastatic sites. As depicted, there may be a correlation between primary sites of cancer and metastatic sites. The model trained using these data may develop weights and connections to infer the correlations for new input images.

Referring now to FIG. 2, depicted is a block diagram of a system 200 for determining primary sites from biomedical image. In overview, the system 200 may include at least one image processing system 205, at least one imaging device 210, and at least one display 215 communicatively coupled with one another via at least one network 220. The image processing system 205 may include at least one model trainer 225, at least one model applier 230, at least one site prediction model 235, and at least one database 240, among others. The database 240 may store, maintain, or otherwise include at least one training dataset 245. Each of the components in the system 200 as detailed herein may be implemented using hardware (e.g., one or more processors coupled with memory) or a combination of hardware and software as detailed herein in Section B.

In further detail, the image processing system 205 itself and the components therein, such as the model trainer 225, the model applier 230, and the site prediction model 235, may have a training mode and a runtime mode (sometimes herein referred to as an evaluation or interference mode). Under the training mode, the image processing system 205 may invoke the model trainer 225 and the model applier 230 to train the site prediction model 235 using the training dataset 245. Under the runtime mode, the image processing system 205 may invoke the model applier 230 to apply the site prediction model 235 to new biomedical images to predict a primary site of a condition in a subject whose tissue is depicted in the biomedical image.

Referring now to FIG. 3, depicted is a block diagram of a training process 300 for the site prediction model 235 in the system 200 for determining primary sites from biomedical images. The process 300 may correspond to or include the operations performed by the image processing system 205 under the training mode. Under the process 300, the model trainer 230 executing on the image processing system 205 may initialize, train, or establish the site prediction model 235. In some embodiments, the model trainer 230 may assign random values to set of weights in the site prediction model 235 as part of the initialization. To train the site prediction model 235, the model trainer 225 may access the database 240 to retrieve, fetch, or identify the training dataset 245. The training dataset 245 may be stored and maintained on the database 240 using at least one data structure (e.g., an array, a matrix, a heap, a list, a tree, or a data object). With the identification, the model trainer 225 may train the site prediction model 235 using the training dataset 245. The training of the site prediction model 235 may be in accordance with supervised (e.g., active or weakly supervised) learning techniques.

The training dataset 325 may include one or more examples. Each example of the training dataset 245 may include at least one image 305, at least one primary site label 310, and at least one image site label 315, among others from a subject 320. The examples in the training dataset 325 may be obtained from multiple subjects 325. In each training dataset 245, the image 305 may be acquired, derived, or otherwise may be of at least one sample 325 from the subject 320. The sample 325 may be a tissue section taken or obtained from the subject 320 (e.g., a human, animal, or flora). The tissue section may include, for example, a muscle tissue, a connective tissue, an epithelial tissue, nervous tissue, or an organ tissue, in the case of a human or animal subject. The sample 325 may be obtained from at least one primary site 330 or at least one secondary site 335 (sometimes referred herein as a metastatic site) of the subject 320. The sample 325 itself may have or include one or more objects with the conditions. For example, the tissue section of the sample 325 may contain tumorous cells or lesions thereon. In this example, the cancerous cells or the lesion may correspond to the object and the condition may correspond to having a tumor or lesion. The primary site 330 may correspond to a location in the subject 320 from which the condition originated. The secondary site 335 may correspond to a location in the subject 320 to which the condition spread. For example, for a subject 320 with lung cancer that spread to the brain, the primary site 330 may be a location within the lung and the secondary site 335 may be a location within the brain.

The image 305 itself may be acquired in accordance with microscopy techniques or a histopathological image preparer, such as using an optical microscope, a confocal microscope, a fluorescence microscope, a phosphorescence microscope, an electron microscope, among others. The image 305 may be, for example, a histological section with a hematoxylin and eosin (H&E) stain, immunostaining, hemosiderin stain, a Sudan stain, a Schiff stain, a Congo red stain, a Gram stain, a Ziehl-Neelsen stain, a Auramine-rhodamine stain, a trichrome stain, a Silver stain, and Wright's Stain, among others. The image 305 may include one or more regions of interest (ROIs). Each ROI may correspond to areas, sections, or boundaries within the sample image 305 that contain, encompass, or include conditions (e.g., features or objects within the image). For example, the sample image 305 may be a whole slide image (WSI) for digital pathology of a tissue section in the sample 325, and the ROIs may correspond to areas with lesions and tumors in the sample tissue. In some embodiments, the ROIs of the sample image 305 may correspond to different conditions. Each condition may define or specify a classification for the ROI. For example, when the image 305 is a WSI of the sample tissue, the conditions may correspond to various histopathological characteristics, such as carcinoma tissue, benign epithelial tissue, stroma tissue, necrotic tissue, and adipose tissue, among others. In some embodiments, the training dataset 245 may include at least one annotation identifying the ROIs in the associated image 305.

In addition, the primary site label 310 may identify the primary site 330 in the subject 320 from which the condition in the sample 325 originated. The image site label 315 may identify a site in the subject 320 from which the sample 325 is obtained. Both the primary site label 310 and the image site label 315 may contain a value (e.g., alphanumeric or numeric) corresponding to one of potential sites in the subject 320. The image site label 315 may be the primary site 330 or the secondary site 335. The primary site label 310 and the image site label 315 may differ or may be the same. When the image 305 is of a sample 325 obtained from the primary site 330, the primary site label 310 and the image site label 315 may be the same. In this case, both the primary site label 310 and the image site label 315 may identify the primary site 330. When the image 305 is of a sample 325 obtained from the secondary site 335, the primary site label 310 and the image site label 315 may differ. In this case, the primary site label 310 may identify the primary site 330 and the image site label 315 may identify the secondary site 335 in the subject 320. The primary site label 310 and the image site label 315 may be inputted or generated by a pathologist or clinician examining the subject 320 or the sample 325. In some embodiments, the image site label 315 may be omitted from the training dataset 245.

In training, the model applier 230 executing on the image processing system 205 may apply the image 305 from the training dataset 245 to the site prediction model 230. The site prediction model 235 may include or have a set of weights (sometimes herein referred to as parameters, kernels, or filters) to process at least one input and produce at least one output. The set of weights in the site prediction model 235 may be arranged, for example, in accordance with a convolutional neural network (CNN) architecture, such as an array of ResNet-50 CNNs. In applying, the model applier 230 may provide or feed the image 305 from each example of the training dataset 245 to the input of the site prediction model 235. In some embodiments, the model applier 230 may feed the entirety of the image 305 to the site prediction model 235. In some embodiments, the model applier 230 may select or identify one or more tiles from the image 305 to input to the site prediction model 235.

Upon feeding, the model applier 230 may process the input image 305 in accordance with the set of weights arranged in the site prediction model 235 to generate at least one output. The output may include one or more predicted primary sites 340. Each predicted primary site 340 may identify the primary site 330 for the condition depicted in the sample 325 of the input image 305. The predicted primary site 340 may include a value (e.g., alphanumeric or numeric) corresponding to one of the sites (e.g., organ) in the subject 320. In some embodiments, the output may include a confidence score for each predicted primary site 340 for the condition. The confidence score may define or indicate a degree of likelihood that the predicted primary site 340 for the condition is the actual primary site 330 for the condition. Details of the architecture and functioning of the site prediction model 235 are described herein below in conjunction with FIGS. 4A-C.

Figure 4A:
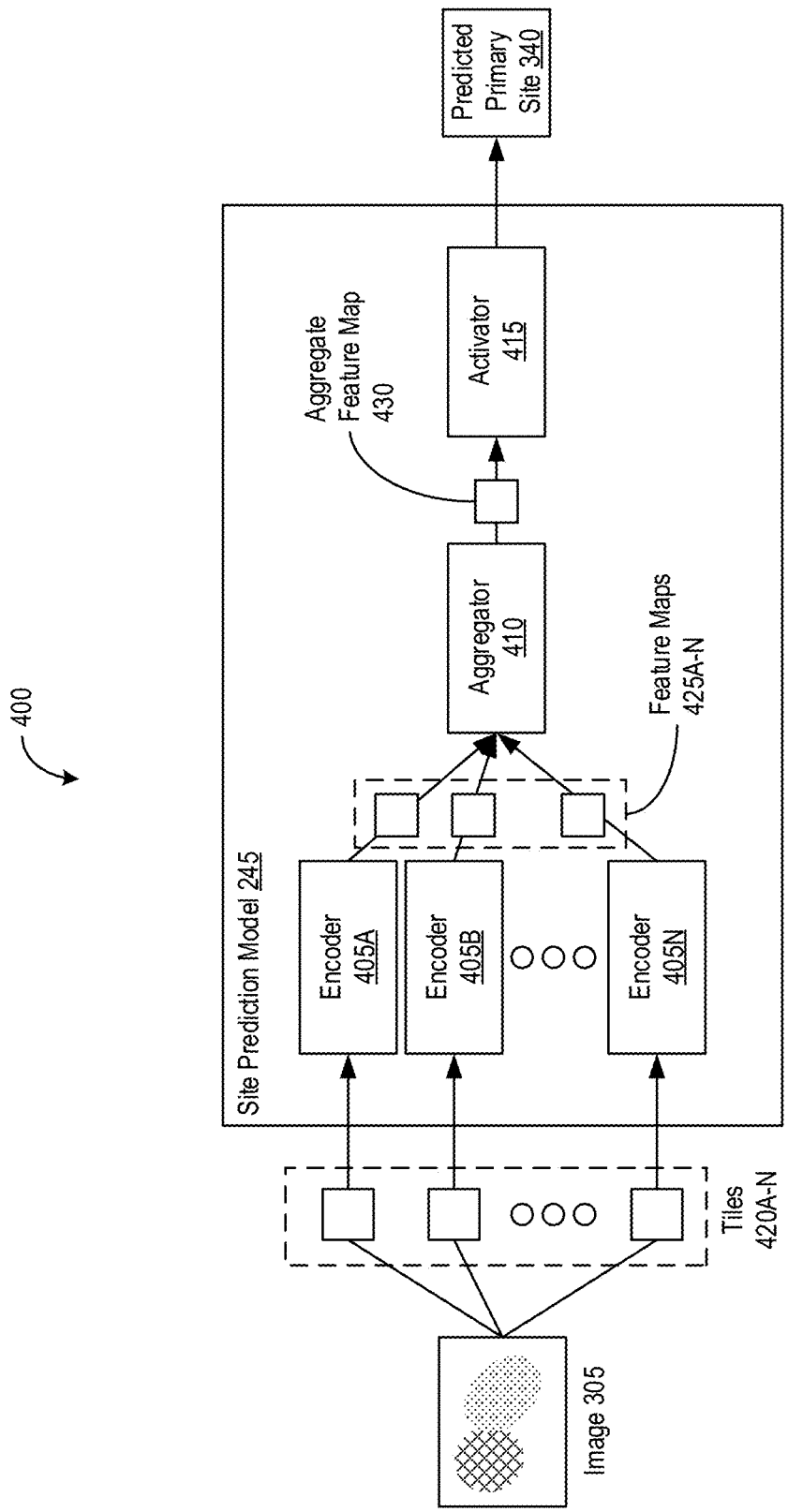
FIG. 4A depicts a block diagram of an architecture of a site prediction model in a system for determining primary sites from biomedical images in accordance with an illustrative embodiment.

Referring now to FIG. 4A, depicted is a block diagram of an architecture 400 of the site prediction model 235 in the system 205 for determining primary sites from biomedical images. Under the architecture 400, the site prediction model 235 may include one or more encoders 405A-N (hereinafter generally encoders 405), at least one aggregator 410, and at least one activator 415 (sometimes herein generally referred to as an activation layer), among others. The set of weights of the site prediction model 235 may be configured, arrayed, or otherwise arranged across the one or more encoders 405, the aggregator 410, and the activator 415, among others. The site prediction model 235 may have one or more inputs and at least one output. The input may include the image 305 or a set of tiles 420A-N (hereinafter generally referred to as tiles 420) from the image 305. The tile 420 may correspond to a portion of the image 305. The output may include the predicted primary site 340 (e.g., as depicted). In some embodiments, the output may include the confidence score for the predicted primary site 340. The inputs and outputs of the encoders 405, the aggregator 410, and the activator 415 may be connected with one another, for example, in the manner depicted.

Each encoder 405 may receive, retrieve, or otherwise identify at least a portion of the image 305 as the input. The input may be the entirety of the image 305 or a corresponding tile 420 from the image 305. In accordance with the weights in the encoder 405, the encoder 405 may process the input. The set of weights in the encoder 405 may be arranged, for example, according to a convolutional neural network (CNN). In some embodiments, the set of weights may be shared amongst the encoder 405. For example, the values and interconnections of the weights within the encoder 405 may be the same throughout the encoders 405 in the site prediction model 235. In some embodiments, the set of weights may be not shared among the encoders 405. For instance, the values or the interconnections of the weights in one encoder 405 may differ or may be independent of the values or the interconnections of the weights in other encoders 405. The encoder 405 may be implemented using the architectures detailed herein in conjunction with FIGS. 4B and 4C. From processing the input, the encoder 405 may produce or generate at least one feature map 425A-N (hereinafter generally referred to as feature maps 425). The feature map 425 may be a lower dimensional representation of the input image 305 or tile 420. For example, the feature map 425 may be a representation of latent features in the input image 305 or respective tile 420. The output of encoder 405 may be provided or fed as the input of the aggregator 410.

The aggregator 410 may in turn receive, retrieve, or otherwise identify the feature maps 425 generated by the corresponding encoders 405. Upon receipt, the aggregator 410 may concatenate or combined the feature maps 425 for input into the set of weights defined in the aggregator 410. The aggregator 410 may process the input in accordance with the set of weights. In some embodiments, the set of weights in the aggregator 410 may be arranged according to a fully convolutional network (FCN). The aggregator 410 may be implemented using the architectures detailed herein in conjunction with FIGS. 4B and 4C. By processing, the aggregator 410 may determine, produce, or otherwise generate at least one aggregate feature map 430. The aggregate feature map 430 may be a lower dimensional representation of the combined set of received feature maps 425. For instance, the aggregate feature map 430 may be a representation of latent features in the combined set of feature maps 425 from the encoders 405. The output of the aggregator 410 may be provided or fed as the input of the activator 415.

The activator 415 may receive, retrieve, or otherwise identify the aggregator feature map 430 generated by the aggregator 401. The activator 415 may process the input aggregate feature map 430 in accordance with the set of weights. The set of weights in the activator 415 may be arranged according to an activation layer, such as a softmax function, a maxout function, a rectified linear unit (ReLU), a linear activation function, a heavyside function, a radial function, or a logistic function, among others. The activator 415 may be implemented using the architectures detailed herein in conjunction with FIGS. 4B and 4C. From processing, the activator 415 may produce or generate at least one output. The output may include at least one predicted primary site 340. The predicted primary site 340 may correspond to a defined site in the subject 320, such as the lung, breast, brain, liver, stomach, thyroid, skin, or any other organ, among others. In some embodiments, the output may include the confidence score for the predicted primary site 340. The confidence score may define or indicate a degree of likelihood that the predicted primary site 340 for the condition is the actual primary site 330 for the condition.

Figure 4B:
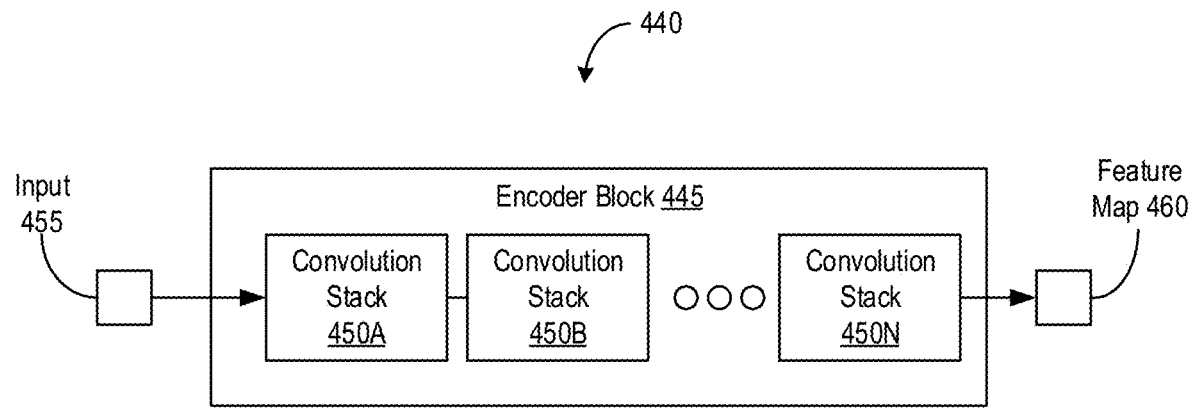
FIG. 4B depicts a block diagram of an architecture of an encoder block in a site prediction model of a system for determining primary sites from biomedical images in accordance with an illustrative embodiment.

Referring now to FIG. 4B, depicted is a block diagram of an architecture 440 of an encoder block 445 in the site prediction model 235 of the system 200 for determining primary sites from biomedical images. The encoder block 445 may be used to implement the individual encoders 405 as well as the aggregator 410 in the site prediction model 245. For example, each encoder 405 and the aggregator 410 may be an instance of the encoder block 445. Under the architecture 440, the encoder block 445 may include one or more convolution stacks 450A-N (hereinafter generally referred to as convolution stacks 450). The encoder block 415 may also include at least one input 455 and at least one output such as a feature map 460. The input 455 and the output feature map 460 may be related via the set of weights defined in the convolution stacks 450. When used to implement the encoder 405, the input 455 of the encoder block 445 may correspond to or include the image 305 or the corresponding tile 420 and the output feature map 460 may correspond to the feature map 425. When used to implement the aggregator 410, the input 455 of the encoder block 445 may correspond to or include the combined set of feature maps 425 and the output 460 may correspond to the aggregate feature map 430. Each convolution stack 450 may define or include the weights the encoder block 445. The set of convolution stacks 450 can be arranged in series (e.g., as depicted) or parallel configuration, or in any combination. In a series configuration, the input of one convolution stacks 450 may include the output of the previous convolution stacks 450 (e.g., as depicted). In parallel configuration, the input of one convolution stacks 450 may include the input of the entire encoder lock 445. Details regarding the architecture of the convolution stack 450 are provided herein below in conjunction with FIG. 4C.

Figure 4C:
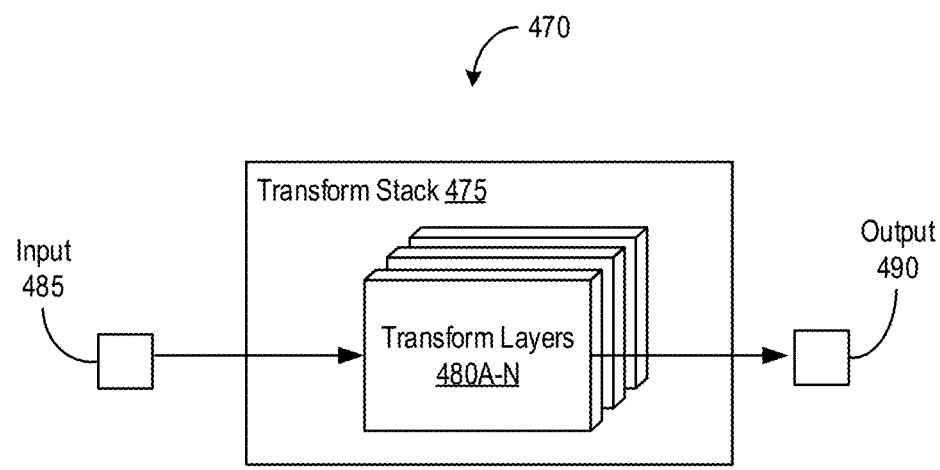
FIG. 4C depicts a block diagram of an architecture of a transform stack in a site prediction model of a system for determining primary sites from biomedical images in accordance with an illustrative embodiment.
Figure 5:
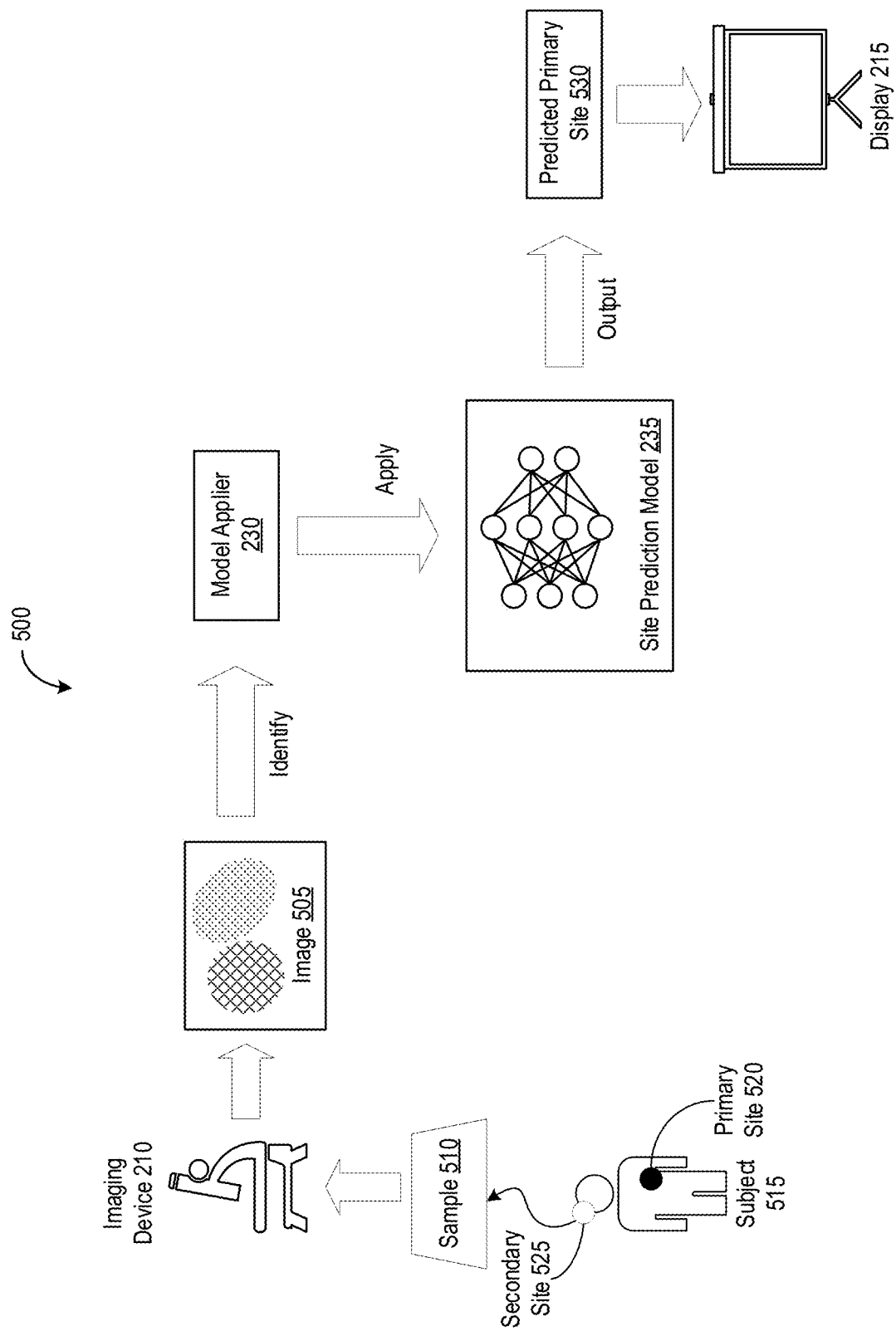

Referring now to FIG. 4C, depicted is a block diagram of an architecture 470 of a transform stack 475 in the site prediction model 235 of the system 200 for determining primary sites from biomedical images. The transform stack 475 may be used to implement the convolution stacks 450 of the encoder blocks 445 used as instances of encoders 405 or aggregators 410 in the site prediction model 235. The transform stack 475 may also be used to implement the activator 415 in the prediction model 235. The transform stack 475 may include one or more transform layers 480A-N (hereinafter generally referred to as transform layers 480). The transform stack 475 also include at least one input 485 and at least one output feature map 490. The input 485 and the output 490 may be related via the set of weights defined in the transform layers 480 of the transform stack 475. When used to implement the activator 415, the input 485 may correspond to the aggregate feature map 430 and the output 490 may correspond to the predicted primary site 340 and the confidence score, among others. The set of transform layers 480 can be arranged in series, with an output of one transform layer 480 fed as an input to a succeeding transform layer 480. Each transform layer 480 may have a non-linear input-to-output characteristic. The transform layer 480 may comprise a convolutional layer, a normalization layer, and an activation layer (e.g., a rectified linear unit (ReLU)), among others. In some embodiments, the set of transform layers 480 may be a convolutional neural network (CNN). For example, the convolutional layer, the normalization layer, and the activation layer (e.g., a softmax function) may be arranged in accordance with CNN.

In the context of FIG. 3, the model trainer 225 may retrieve, obtain, or otherwise identify the output produced by the site prediction model 235 from the application of the image 305. The output may include, for example, the at least one predicted primary site 340 and the confidence score for the predicted primary site 340, among others. In conjunction, the model trainer 225 may identify the input image 305, the primary site label 310, or the image site label 315 of the example in the training dataset 245 used to generate the predicted primary site 340. In some embodiments, the model trainer 225 may identify the primary site label 310 identified in the example of the training dataset 245 used to generate the predicted primary site 340. In some embodiments, the model trainer 225 may identify the image site label 315 identified in the same example.

With the identification, the model trainer 225 may compare the predicted primary site 340 generated by the site prediction model 235 with the primary site label 310 as identified in the example from the training dataset 245. When there are multiple predicted primary sites 340 outputted by the site prediction model 235, the model trainer 225 may select or identify the predicted primary site 340 with the highest confidence score for training purposes. In some embodiments, the model trainer 225 may compare the value included in the predicted primary site 340 with the value indicated by the primary site label 310.

From comparing, the model trainer 225 may determine whether the predicted primary site 340 generated by the site prediction model 235 is correct. When the predicted primary site 340 matches the primary site label 310, the model trainer 225 may determine that the predicted primary site 340 is correct. In some embodiments, the model trainer 225 may identify the example in the training dataset 245 used to produce the predicted primary site 340 as correctly determined. The model trainer 225 may also exclude the example from the training dataset 245 from a retraining dataset. Conversely, when the predicted primary site 340 does not match the primary site label 310, the model trainer 225 may determine that the predicted primary site 340 is incorrect. In some embodiments, the model trainer 225 may identify the example in the training dataset 245 used to produce the predicted primary site 340 as incorrect determined (sometimes herein referred to as a hard example). The model trainer 225 may include the example from the training dataset 245 in the retraining dataset.

In some embodiments, the model trainer 225 may factor in the image site label 315 of the example in the training dataset 325 in including examples in the retraining dataset. The model trainer 225 may identify a number of examples in the retraining dataset with the image site label 315 for a particular site in the subject 320. The model trainer 225 may compare the number of examples to a threshold. The threshold may define a value for the number of examples at which to include all examples with the same image site label 315 into the retraining dataset. When the number of examples is greater than or equal to the threshold, the model trainer 225 may include all the examples from the training dataset 245 with the same image site label 315 into the retraining dataset. Otherwise, when the number of examples is less than the threshold, the model trainer 225 may maintain the current number of examples in the retraining dataset.

Based on the comparisons, the model trainer 225 may calculate, generate, or otherwise determine at least one loss metric (sometimes herein referred to as an error metric) for updating the weights of the site prediction model 235. The loss metric may be determined using many outputs from the site prediction model 235 generated using many examples from the training dataset 245. The loss metric may indicate a degree of deviation of the output (e.g., the predicted primary site 340) from the site prediction model 235 from the expected result (e.g., the primary site label 310) as indicated in the training dataset 245. For example, the loss metric may measure a classification loss from incorrect classifications of the images 305 into one of the sites besides the correct site as identified in the primary site label 310. The loss metric may be calculated in accordance with any number of loss functions, such as a Huber loss, norm loss (e.g., L1 or L2), mean squared error (MSE), a quadratic loss, and a cross-entropy loss, among others. In general, the higher the loss metric, the more the output may have deviated from the expected result of the input. Conversely, the lower the loss metric, the lower the output may have deviated from the expected result. In some embodiments, an example may be included in the retraining dataset when the loss metric for the predicted primary site 340 generated using the example is greater than a threshold. The threshold may define or delineate a value for the loss metric at which to include the corresponding example into the retraining dataset. In some embodiments, the model trainer 225 may combine the results of the comparisons with respect to the output and the training dataset 245 to calculate the loss metric.

Using the loss metric, the model trainer 225 may modify, set, or otherwise update one or more weights in the site prediction model 235. The updating of the weights may be across the encoders 405, the aggregator 410, and the activator 415 within the site prediction model 245. The updating of weights may be in accordance with an optimization function (or an objective function) for the site prediction model 235. The optimization function may define one or more rates or parameters at which the weights of the site prediction network 235 are to be updated. The updating of the kernels in the site prediction model 235 may be repeated until a convergence condition.

In some embodiments, the model trainer 225 may use the retraining dataset to continue training the site prediction model 235. The retraining dataset may include one or examples for which the site prediction model 235 previously produced an incorrected predicted primary site 340. The training of the prediction model 235 using the retraining dataset may be similar to training using the original dataset 245 as described above. For example, the model applier 230 may reapply the image 305 from each example included in the retraining dataset to the site prediction model 235. Using the predicted primary site 340 produced by the site prediction model 235, the model trainer 225 may calculate another loss metric and update the weights of the site prediction model 235 accordingly.

Upon convergence, the model trainer 225 may store and maintain the set of weights of the site prediction model 235. The convergence may correspond to a change in the value of the weights in the site prediction model 235 is below a threshold value. The set of weights of the site prediction model 235 may be stored using one or more data structures, such as an array, a matrix, a heap, a list, a tree, or a data object, among others. In some embodiments, the model trainer 225 may store the set of weights of the site prediction model 235 in the database 240.

Referring now to FIG. 5, depicted is a block diagram of an inference process 500 for the site prediction model 235 in the system 200 for determining primary sites from biomedical images. The process 500 may correspond to or include the operations performed by the image processing system 205 under the runtime mode. Under the process 500, the imaging device 210 may scan, obtain, or otherwise acquire at least one image 505 of at least one sample 510 from a subject 515. The image 505 may be similar to the image 305 described above. The sample 510 may be a tissue section taken or obtained from the subject 515. The sample 510 may be obtained from at least one primary site 520 or at least one secondary site 525 (sometimes referred herein as a metastatic site) of the subject 515. The sample 510 itself may have or include one or more objects with the conditions. For example, the tissue section of the sample 510 may contain tumorous cells or lesions thereon. The primary site 520 may correspond to a location in the subject 515 from which the condition originated. The secondary site 525 may correspond to a location in the subject 515 to which the condition spread. For example, for a subject 515 with lung cancer that spread to the brain, the primary site 520 may be a location within the lung and the secondary site 525 may be a location within the brain. The image 505 may be acquired in accordance with microscopy techniques or a histopathological imaging. Upon acquisition, the imaging device 210 may send, transmit, or otherwise provide the acquired image 505 to the imaging processing system 205.

The model applier 230 may in turn retrieve, receive, or otherwise identify the image 505 from the imaging device 210. The model applier 230 may provide or feed the image 505 to the input of the site prediction model 235. In some embodiments, the model applier 230 may feed the entirety of the image 505 to the site prediction model 235. In some embodiments, the model applier 230 may select or identify one or more tiles (e.g., similar to tiles 420) from the image 505 to input to the site prediction model 235. Upon feeding, the model applier 230 may process the input image 505 in accordance with the set of weights arranged in the site prediction model 235 to generate at least one output. The output may include one or more predicted primary sites 530. Each predicted primary site 530 may identify the primary site 520 for the condition depicted in the sample 325 of the input image 505. The predicted primary site 530 may include a value (e.g., alphanumeric or numeric) corresponding to one of the sites (e.g., organ) in the subject 515. In some embodiments, the output may include a confidence score for each predicted primary site 530 for the condition. The confidence score may define or indicate a degree of likelihood that the predicted primary site 530 for the condition is the actual primary site 520 for the condition. In some embodiments, the model applier 230 may rank the predicted primary sites 530 by confidence scores.

With the generation, the model applier 230 may store and maintain an association between the image 505 and the output from the site prediction model 235. The output may include one or more of the predicted primary sites 430 and the corresponding confidence scores. The association may be stored on the database 240 using one or more data structures. In addition, the model applier 230 may send, transmit, or otherwise provide the output from the site prediction model 235 to the display 215 for presentation or rendering. In some embodiments, the model applier 230 may also provide the association between image 505 and the corresponding output to the display 215. The display 215 may render or present the output from the site prediction model 235, such as the predicted primary sites 530 and the confidence scores. In some embodiments, the display 215 may also present the image 505 along with the output from the site prediction model 235. The display 215 may present the information from the image processing system 205 in a graphical user interface. For example, the graphical user interface may provide the image 505, the predicted primary sites 530 ranked by the confidence scores, and the confidence scores themselves. The graphical user interface may also include other information regarding the subject 515 or the sample 510 from which the image 505 is obtained. In this manner, the site prediction model 235 of the image processing system 205 may be able to learn the morphological latent features from images 505 to determine predicted primary sites 530 of images 505 of samples 510 from the subject 515. The image 505 may have been from the secondary site 525 or the actual primary site 520 itself.

Figure 6A:
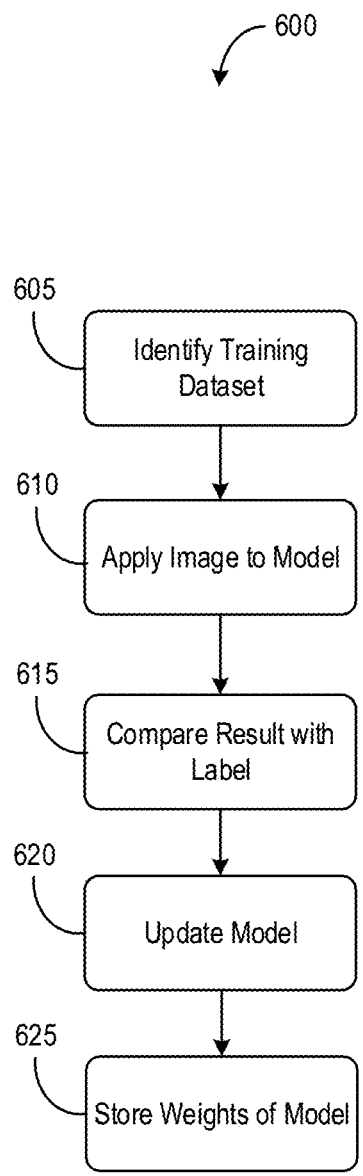
FIG. 6A depicts a flow diagram of a method of training models to determine primary sites, in accordance with an illustrative embodiment.

Referring now to FIG. 6A, depicted is a flow diagram of a method 600 of training models to determine primary sites. The method 600 may be performed by or implemented using the system 300 described herein in conjunction with FIGS. 2-5 or the system 700 detailed herein in conjunction in Section B. In brief overview, under the method 600, a computing system (e.g., the image processing system 205) may identify a training dataset (e.g., the training dataset 245) (605). The computing system may apply an image (e.g., the image 305) to a model (e.g., the site prediction model 235) (610). The computing system may compare a result (e.g., the predicted primary site 340) with a label (e.g., the primary site label 310) (615). The computing system may update the model (620). The computing system may store weights of the model (625).

Figure 6B:
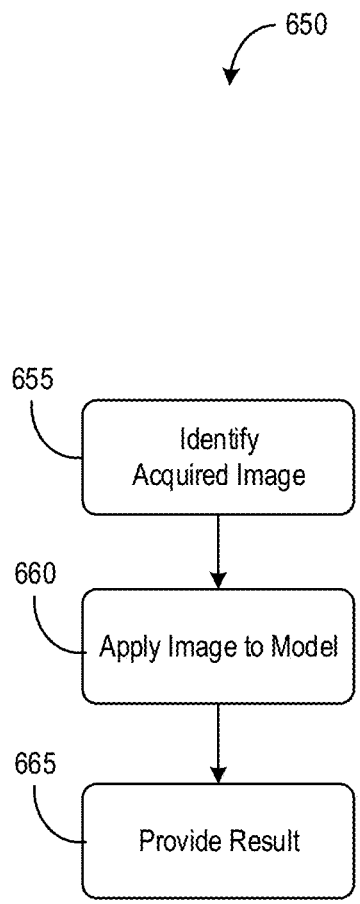
FIG. 6B depicts a flow diagram of a method of applying models to determine primary sites, in accordance with an illustrative embodiment.
Figure 7:
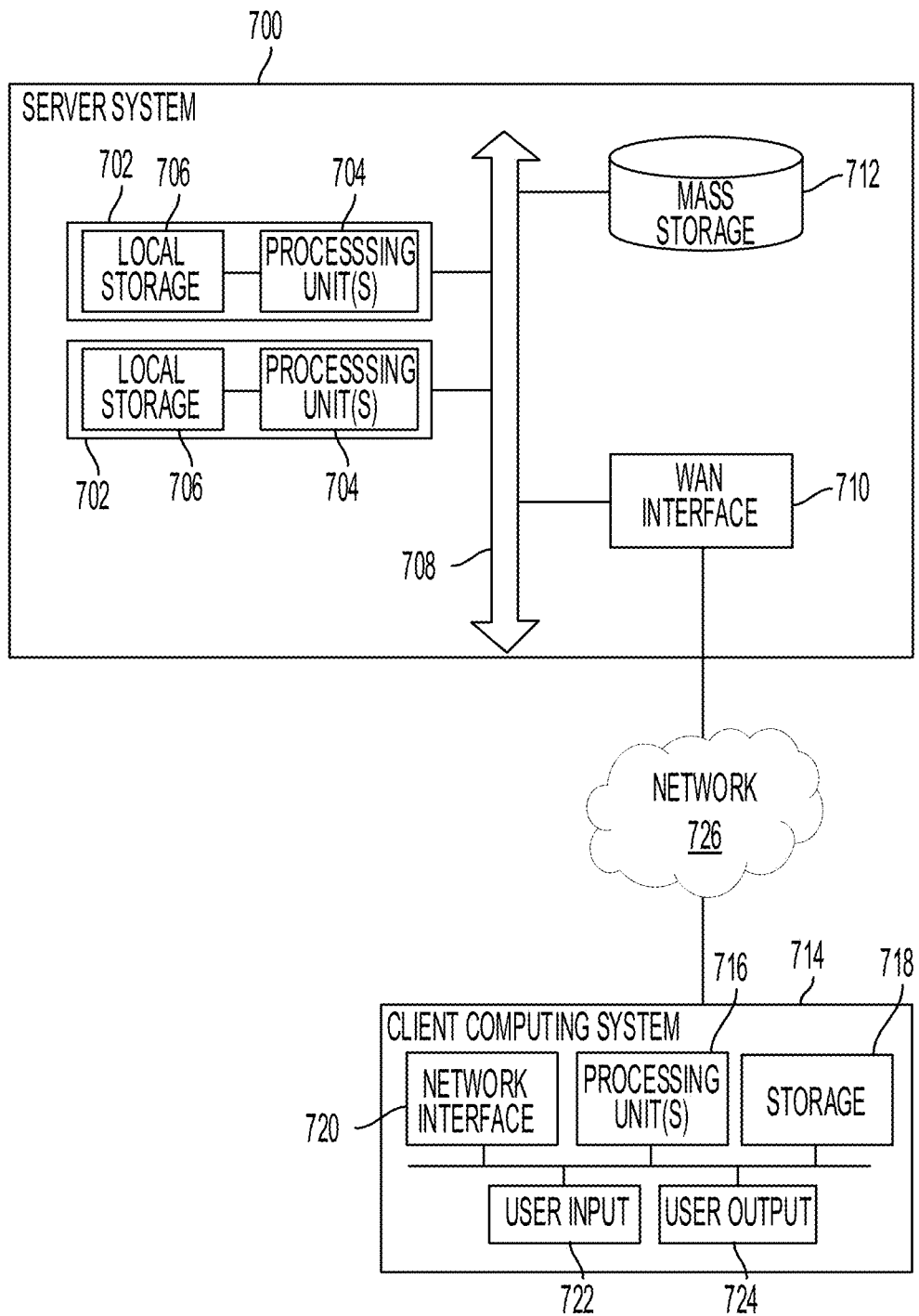

Referring now to FIG. 6B, depicted is a flow diagram of a method 650 of applying models to determine primary sites. The method 650 may be performed by or implemented using the system 300 described herein in conjunction with FIGS. 2-5 or the system 700 detailed herein in conjunction in Section B. Under the method 650, a computing system (e.g., the image processing system 205) may identify an acquired image (e.g., the image 505) (655). The computing system may apply the image to a model (e.g., the site prediction model 235) (660). The computing system may provide a result (e.g., the predicted primary site 530) (665).

B. Computing and Network Environment

Various operations described herein can be implemented on computer systems. FIG. 7 shows a simplified block diagram of a representative server system 700, client computer system 714, and network 726 usable to implement certain embodiments of the present disclosure. In various embodiments, server system 700 or similar systems can implement services or servers described herein or portions thereof. Client computer system 714 or similar systems can implement clients described herein. The system 300 described herein can be similar to the server system 700. Server system 700 can have a modular design that incorporates a number of modules 702 (e.g., blades in a blade server embodiment); while two modules 702 are shown, any number can be provided. Each module 702 can include processing unit(s) 704 and local storage 706.

Processing unit(s) 704 can include a single processor, which can have one or more cores, or multiple processors. In some embodiments, processing unit(s) 704 can include a general-purpose primary processor as well as one or more special-purpose co-processors such as graphics processors, digital signal processors, or the like. In some embodiments, some or all processing units 704 can be implemented using customized circuits, such as application specific integrated circuits (ASICs) or field programmable gate arrays (FPGAs). In some embodiments, such integrated circuits execute instructions that are stored on the circuit itself. In other embodiments, processing unit(s) 704 can execute instructions stored in local storage 706. Any type of processors in any combination can be included in processing unit(s) 704.

Local storage 706 can include volatile storage media (e.g., DRAM, SRAM, SDRAM, or the like) and/or non-volatile storage media (e.g., magnetic or optical disk, flash memory, or the like). Storage media incorporated in local storage 706 can be fixed, removable or upgradeable as desired. Local storage 706 can be physically or logically divided into various subunits such as a system memory, a read-only memory (ROM), and a permanent storage device. The system memory can be a read-and-write memory device or a volatile read-and-write memory, such as dynamic random-access memory. The system memory can store some or all of the instructions and data that processing unit(s) 704 need at runtime. The ROM can store static data and instructions that are needed by processing unit(s) 704. The permanent storage device can be a non-volatile read-and-write memory device that can store instructions and data even when module 702 is powered down. The term "storage medium" as used herein includes any medium in which data can be stored indefinitely (subject to overwriting, electrical disturbance, power loss, or the like) and does not include carrier waves and transitory electronic signals propagating wirelessly or over wired connections.

In some embodiments, local storage 706 can store one or more software programs to be executed by processing unit(s) 704, such as an operating system and/or programs implementing various server functions such as functions of the system 500 of FIG. 5 or any other system described herein, or any other server(s) associated with system 500 or any other system described herein.

"Software" refers generally to sequences of instructions that, when executed by processing unit(s) 704 cause server system 700 (or portions thereof) to perform various operations, thus defining one or more specific machine embodiments that execute and perform the operations of the software programs. The instructions can be stored as firmware residing in read-only memory and/or program code stored in non-volatile storage media that can be read into volatile working memory for execution by processing unit(s) 704. Software can be implemented as a single program or a collection of separate programs or program modules that interact as desired. From local storage 706 (or non-local storage described below), processing unit(s) 704 can retrieve program instructions to execute and data to process in order to execute various operations described above.

In some server systems 700, multiple modules 702 can be interconnected via a bus or other interconnect 708, forming a local area network that supports communication between modules 702 and other components of server system 700. Interconnect 708 can be implemented using various technologies including server racks, hubs, routers, etc.

A wide area network (WAN) interface 710 can provide data communication capability between the local area network (interconnect 708) and the network 726, such as the Internet. Technologies can be used, including wired (e.g., Ethernet, IEEE 702.3 standards) and/or wireless technologies (e.g., Wi-Fi, IEEE 702.11 standards).

In some embodiments, local storage 706 is intended to provide working memory for processing unit(s) 704, providing fast access to programs and/or data to be processed while reducing traffic on interconnect 708. Storage for larger quantities of data can be provided on the local area network by one or more mass storage subsystems 712 that can be connected to interconnect 708. Mass storage subsystem 712 can be based on magnetic, optical, semiconductor, or other data storage media. Direct attached storage, storage area networks, network-attached storage, and the like can be used. Any data stores or other collections of data described herein as being produced, consumed, or maintained by a service or server can be stored in mass storage subsystem 712. In some embodiments, additional data storage resources may be accessible via WAN interface 710 (potentially with increased latency).

Server system 700 can operate in response to requests received via WAN interface 710. For example, one of modules 702 can implement a supervisory function and assign discrete tasks to other modules 702 in response to received requests. Work allocation techniques can be used. As requests are processed, results can be returned to the requester via WAN interface 710. Such operation can generally be automated. Further, in some embodiments, WAN interface 710 can connect multiple server systems 700 to each other, providing scalable systems capable of managing high volumes of activity. Other techniques for managing server systems and server farms (collections of server systems that cooperate) can be used, including dynamic resource allocation and reallocation.

Server system 700 can interact with various user-owned or user-operated devices via a wide-area network such as the Internet. An example of a user-operated device is shown in FIG. 7 as client computing system 714. Client computing system 714 can be implemented, for example, as a consumer device such as a smartphone, other mobile phone, tablet computer, wearable computing device (e.g., smart watch, eyeglasses), desktop computer, laptop computer, and so on.

For example, client computing system 714 can communicate via WAN interface 710. Client computing system 714 can include computer components such as processing unit(s) 716, storage device 718, network interface 720, user input device 722, and user output device 724. Client computing system 714 can be a computing device implemented in a variety of form factors, such as a desktop computer, laptop computer, tablet computer, smartphone, other mobile computing device, wearable computing device, or the like.

Processor 716 and storage device 718 can be similar to processing unit(s) 704 and local storage 706 described above. Suitable devices can be selected based on the demands to be placed on client computing system 714; for example, client computing system 714 can be implemented as a "thin" client with limited processing capability or as a high-powered computing device. Client computing system 714 can be provisioned with program code executable by processing unit(s) 716 to enable various interactions with server system 700.

Network interface 720 can provide a connection to the network 726, such as a wide area network (e.g., the Internet) to which WAN interface 710 of server system 700 is also connected. In various embodiments, network interface 720 can include a wired interface (e.g., Ethernet) and/or a wireless interface implementing various RF data communication standards such as Wi-Fi, Bluetooth, or cellular data network standards (e.g., 3G, 4G, LTE, etc.).

User input device 722 can include any device (or devices) via which a user can provide signals to client computing system 714; client computing system 714 can interpret the signals as indicative of particular user requests or information. In various embodiments, user input device 722 can include any or all of a keyboard, touch pad, touch screen, mouse or other pointing device, scroll wheel, click wheel, dial, button, switch, keypad, microphone, and so on.

User output device 724 can include any device via which client computing system 714 can provide information to a user. For example, user output device 724 can include a display to display images generated by or delivered to client computing system 714. The display can incorporate various image generation technologies, e.g., a liquid crystal display (LCD), light-emitting diode (LED) including organic light-emitting diodes (OLED), projection system, cathode ray tube (CRT), or the like, together with supporting electronics (e.g., digital-to-analog or analog-to-digital converters, signal processors, or the like). Some embodiments can include a device such as a touchscreen that function as both input and output device. In some embodiments, other user output devices 724 can be provided in addition to or instead of a display. Examples include indicator lights, speakers, tactile "display" devices, printers, and so on.

Some embodiments include electronic components, such as microprocessors, storage and memory that store computer program instructions in a computer readable storage medium. Many of the features described in this specification can be implemented as processes that are specified as a set of program instructions encoded on a computer readable storage medium. When these program instructions are executed by one or more processing units, they cause the processing unit(s) to perform various operation indicated in the program instructions. Examples of program instructions or computer code include machine code, such as is produced by a compiler, and files including higher-level code that are executed by a computer, an electronic component, or a microprocessor using an interpreter. Through suitable programming, processing unit(s) 704 and 716 can provide various functionality for server system 700 and client computing system 714, including any of the functionality described herein as being performed by a server or client, or other functionality.

It will be appreciated that server system 700 and client computing system 714 are illustrative and that variations and modifications are possible. Computer systems used in connection with embodiments of the present disclosure can have other capabilities not specifically described here. Further, while server system 700 and client computing system 714 are described with reference to particular blocks, it is to be understood that these blocks are defined for convenience of description and are not intended to imply a particular physical arrangement of component parts. For instance, different blocks can be but need not be located in the same facility, in the same server rack, or on the same motherboard. Further, the blocks need not correspond to physically distinct components. Blocks can be configured to perform various operations, e.g., by programming a processor or providing appropriate control circuitry, and various blocks might or might not be reconfigurable depending on how the initial configuration is obtained. Embodiments of the present disclosure can be realized in a variety of apparatus including electronic devices implemented using any combination of circuitry and software.

While the disclosure has been described with respect to specific embodiments, one skilled in the art will recognize that numerous modifications are possible. Embodiments of the disclosure can be realized using a variety of computer systems and communication technologies including but not limited to specific examples described herein. Embodiments of the present disclosure can be realized using any combination of dedicated components and/or programmable processors and/or other programmable devices. The various processes described herein can be implemented on the same processor or different processors in any combination. Where components are described as being configured to perform certain operations, such configuration can be accomplished, e.g., by designing electronic circuits to perform the operation, by programming programmable electronic circuits (such as microprocessors) to perform the operation, or any combination thereof. Further, while the embodiments described above may make reference to specific hardware and software components, those skilled in the art will appreciate that different combinations of hardware and/or software components may also be used and that particular operations described as being implemented in hardware might also be implemented in software or vice versa.

Computer programs incorporating various features of the present disclosure may be encoded and stored on various computer readable storage media; suitable media include magnetic disk or tape, optical storage media such as compact disk (CD) or DVD (digital versatile disk), flash memory, and other non-transitory media. Computer readable media encoded with the program code may be packaged with a compatible electronic device, or the program code may be provided separately from electronic devices (e.g., via Internet download or as a separately packaged computer-readable storage medium).

Thus, although the disclosure has been described with respect to specific embodiments, it will be appreciated that the disclosure is intended to cover all modifications and equivalents within the scope of the following claims.

What is claimed is:

1. A method of determining primary sites from biomedical images, comprising:
    identifying, by a computing system, a first biomedical image of a first sample obtained from a secondary site associated with a condition in a first subject, the condition originating from a primary site and spreading to the secondary site, the primary site corresponding to a first organ and the secondary site corresponding to a second organ different from the first organ of the first subject;

determining, by the computing system, the primary site corresponding to the first organ from which the condition originated by applying the first biomedical image to a site prediction model comprising a plurality of weights, the site prediction model trained using a training dataset having a plurality of examples, each example comprising:
- i) a respective biomedical image of a respective sample obtained from one of a respective primary site where a respective condition originated or a respective secondary site to which the respective condition spread,
- ii) a first label identifying one of the respective primary site or the respective secondary site from which the respective sample was obtained, and
- iii) a second label identifying the respective primary site where the respective condition originated; and storing, by the computing system, for the first subject, an association between the first biomedical image and the primary site determined using the site prediction model.

2. The method of claim 1, further comprising providing, by the computing system, the association between the first biomedical image and the primary site.

3. The method of claim 1, wherein applying further comprises applying the first biomedical image to the site prediction model to determine a plurality of candidate primary sites for the condition in the first subject.

4. The method of claim 1, wherein applying further comprises applying the first biomedical image to the site prediction model to determine a confidence score for the primary site for the condition.

5. The method of claim 1, wherein applying further comprises applying the first biomedical image to the site prediction model to determine a ranking for a plurality of candidate primary sites.

6. The method of claim 1, wherein identifying the first biomedical image further comprises obtaining the first biomedical image of the first sample via a histological image preparer.

7. The method of claim 1, wherein the plurality of weights in the site prediction model is arranged into (i) a plurality of convolution blocks to generate a plurality of feature maps from the first biomedical image and (ii) an activation layer to determine the primary site for the condition based on the plurality of feature maps.

8. A method of training models to determine primary sites from biomedical images, comprising:

identifying, by a computing system, a training dataset having a plurality of examples, each example of the plurality of examples comprising:
- i) a biomedical image of a respective sample obtained from one of a respective primary site where a respective condition originated in a respective subject or a respective secondary site of the condition to which the respective condition spread in the respective subject, the respective primary site corresponding to a respective first organ and the respective secondary site corresponding to a respective second organ different from the respective first organ of the respective subject,
- ii) a first label identifying one of the respective primary site or the respective secondary site from which the respective sample was obtained, and
- iii) a second label identifying the primary site where the respective condition originated;

applying, by the computing system, the biomedical image in each of the plurality of examples of the training dataset to a site prediction model comprising a plurality of weights to determine the primary site corresponding to the first organ from which the respective condition of the respective sample originated in the respective subject;

comparing, by the computing system, for each example of the plurality of examples in the training dataset, the primary site identified in the second label of the example and the primary site determined by the site prediction model for the respective subject;

updating, by the computing system, at least one of the plurality of weights in the site prediction model based on the comparison between the primary site identified in the second label of each example and the primary site determined by the site prediction model; and storing, by the computing system, in one or more data structures, the plurality of weights in the site prediction model.

9. The method of claim 8, further comprising applying, by the computing system, an acquired biomedical image of a second sample to the site prediction model to determine a primary site for the second sample.

10. The method of claim 8, further comprising reapplying, by the computing system, the biomedical image of at least one example of the plurality of examples to the site prediction model, responsive to determining that a loss metric for the at least one example exceeds a threshold.

11. The method of claim 8, wherein updating further comprises updating at least one of the plurality of weights in the site prediction model using a classification loss determined based on the comparison.

12. The method of claim 8, wherein applying further comprises applying the biomedical image in each of the plurality of examples of the training dataset to determine a plurality of candidate primary sites for the respective condition.

13. The method of claim 8, wherein applying further comprises applying the biomedical image in each of the plurality of examples of the training dataset to determine a confidence score for the primary site for the respective condition.

14. The method of claim 8, wherein the plurality of weights in the site prediction model is arranged into (i) a plurality of convolution blocks to generate a plurality of feature maps from the biomedical image and (ii) an activation layer to determine the primary site for the condition based on the plurality of feature maps.

15. A system for determining primary sites from biomedical images of metastatic sites, comprising:

a computing system having one or more processors coupled with memory, configured to:
identify a first biomedical image of a first sample obtained from a secondary site associated with a condition in a first subject, the condition originating from a primary site and spreading to the secondary site, the primary site corresponding to a first organ and the secondary site corresponding to a second organ different from the first organ of the first subject;

determine the first primary site corresponding to the first organ from which the condition originated by applying the first biomedical image to a site prediction model comprising a plurality of weights, the site prediction model trained using a training dataset having a plurality of examples, each example comprising:
  i) a respective biomedical image of a respective sample obtained from one of a respective primary site where a respective condition originated or a respective secondary site to which the respective condition spread,
  ii) a first label identifying one of the respective primary site or the respective secondary site from which the respective sample was obtained, and
  iii) a second label identifying respective primary site where the respective condition originated; and
store, for the first subject, an association between the first biomedical image and the primary site determined using the site prediction model.

16. The system of claim 15, wherein the computing system is further configured to provide the association between the first biomedical image and the primary site.

17. The system of claim 15, wherein the computing system is further configured to apply the first biomedical image to the site prediction model to determine a plurality of candidate primary sites for the condition in the first subject.

18. The system of claim 15, wherein the computing system is further configured to apply the first biomedical image to the site prediction model to determine a confidence score for the primary site for the condition.

19. The system of claim 15, wherein the computing system is further configured to apply the first biomedical image to the site prediction model to determine a ranking for a plurality of candidate primary sites.

20. The system of claim 15, wherein the plurality of weights in the site prediction model is arranged into (i) a plurality of convolution blocks to generate a plurality of feature maps from the first biomedical image and (ii) an activation layer to determine the primary site for the condition based on the plurality of feature maps.

* * * * *